US009730765B2

United States Patent
Mangelberger et al.

(10) Patent No.: US 9,730,765 B2
(45) Date of Patent: Aug. 15, 2017

(54) MEDICAL OR DENTAL HANDPIECE WITH INDUCTIVE COUPLING

(75) Inventors: Michael Mangelberger, St. Georgen (AT); Christian Pruckner, Vienna (AT); Gunter Teufelberger, Bürmoos (AT); Hannes Wagner, Salzburg (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 799 days.

(21) Appl. No.: 12/732,017

(22) Filed: Mar. 25, 2010

(65) Prior Publication Data

US 2010/0248177 A1    Sep. 30, 2010

(30) Foreign Application Priority Data

Mar. 26, 2009  (EP) .................................. 09004327
May 7, 2009    (EP) .................................. 09006196

(51) Int. Cl.
| | |
|---|---|
| A61C 1/00 | (2006.01) |
| A61C 1/12 | (2006.01) |
| A61C 1/14 | (2006.01) |
| A61C 3/02 | (2006.01) |

(52) U.S. Cl.
CPC ................ A61C 1/12 (2013.01); A61C 1/145 (2013.01); A61C 3/02 (2013.01)

(58) Field of Classification Search
CPC   H02J 5/005; H02J 7/025; H01F 38/14; A61C 1/141; A61C 1/185; A61C 1/12
USPC ......... 433/114–116, 126–131, 133; 606/167, 606/79–80; 307/104; 279/131; 408/16, 408/124, 226, 239 R; 464/52–53
See application file for complete search history.

(56) References Cited

U.S. PATENT DOCUMENTS

| | | | |
|---|---|---|---|
| 3,731,385 A | 5/1973 | Farber et al. | |
| 4,110,908 A | 9/1978 | Cranston | |
| 5,584,689 A | * 12/1996 | Loge ...................... | A61C 1/141 433/127 |
| 6,563,087 B1 | * 5/2003 | Yokoyama ............. | B23K 3/033 219/240 |

(Continued)

FOREIGN PATENT DOCUMENTS

| | | |
|---|---|---|
| DE | 10045116 | 3/2002 |
| JP | 2004208922 | 7/2004 |

(Continued)

OTHER PUBLICATIONS

Search Report for EP09006196 (mailed Nov. 28, 2013).

*Primary Examiner* — Matthew Nelson
(74) *Attorney, Agent, or Firm* — Klarquist Sparkman, LLP

(57) ABSTRACT

Various medical or dental handpieces having at least one coil for inductive coupling with a second coil and methods for using these handpieces for the transmission of at least one of power, operational data and identification data are described. Also various tool-holding/releasing devices for medical or dental handpieces are described, having at least one shaped element penetrating through a bore in a hollow shaft for accommodating a tool and protruding through the bore into the hollow shaft, a movably arranged locking sleeve cooperating with the shaped element and an operating element for moving the locking sleeve. Some of these tool-holding/releasing devices allow the insertion of the tool into the hollow shaft with different insertion depths.

22 Claims, 11 Drawing Sheets

(56) References Cited

U.S. PATENT DOCUMENTS

| | | | |
|---|---|---|---|
| 6,585,628 B1* | 7/2003 | Tsung | B23C 5/00 408/16 |
| 7,887,559 B2* | 2/2011 | Deng | A61B 17/32002 15/21.1 |
| 2003/0093103 A1* | 5/2003 | Malackowski | A61B 34/20 606/170 |
| 2004/0133189 A1 | 7/2004 | Sakurai | |
| 2004/0267297 A1* | 12/2004 | Malackowski | A61B 34/20 606/167 |
| 2006/0159533 A1* | 7/2006 | Zeiler | B23B 49/006 408/226 |
| 2007/0065774 A1* | 3/2007 | Pernot | A61C 1/08 433/126 |
| 2007/0234493 A1* | 10/2007 | Hilscher | A61C 17/22 15/22.2 |
| 2008/0010771 A1 | 1/2008 | Hilscher et al. | |
| 2008/0132882 A1* | 6/2008 | DeMaria | A61B 17/16 606/1 |
| 2008/0211634 A1* | 9/2008 | Hopkins | A61B 1/00016 340/10.1 |
| 2008/0293008 A1* | 11/2008 | Regere | A61C 1/0015 433/119 |
| 2009/0131922 A1* | 5/2009 | Dewey | A61B 18/203 606/9 |
| 2009/0175694 A1* | 7/2009 | Craig | B23B 51/00 407/37 |
| 2011/0089248 A1* | 4/2011 | Deng | A61B 17/32002 235/492 |

FOREIGN PATENT DOCUMENTS

| | | |
|---|---|---|
| JP | 2004524100 | 8/2004 |
| JP | 2004537367 | 12/2004 |

\* cited by examiner

MEDICAL OR DENTAL HANDPIECE WITH INDUCTIVE COUPLING

CROSS REFERENCE TO RELATED APPLICATION

The present application claims priority from European Patent Application No. 09004327.4, filed Mar. 26, 2009, now abandoned, and from pending European Patent Application No. 09006196.1, filed May 7, 2009, which are both incorporated herein by reference.

BACKGROUND

Field

The present application relates to a medical or dental handpiece having a coil for inductive power and/or data exchange.

Description of Prior Art

Such a handpiece is known from US Patent Application US 2003/0093103 A1. The handpiece comprises an outer shell, in which a bore is provided for insertion of a treatment tool. In addition, a drive shaft couplable with the treatment tool is provided in the bore, so that a rotational movement may be induced to the treatment tool. A memory unit comprising a memory, e.g., for identification data or operating data of the treatment tool and a coil connected to the memory is provided on the treatment tool. The coil of the memory unit is inductively coupled to another coil in the handpiece, so that data and power supply for the memory can be transferred from the handpiece to the memory unit of the treatment tool and data can be transferred from the memory to the handpiece.

The coil of the handpiece is arranged on the front end of the handpiece in a receptacle or in a setback of the outer shell. The receptacle or setback for the coil is connected to the environment via gaps and/or the bore for insertion of the treatment tool, so that there is the risk that treatment fluids, particles or other soiling may reach the coil through the gaps or bores, impairing its function and thus hindering or interrupting the overall data and power transfer. To reduce this risk, a plurality of sealing means, such as O-rings, adhesives, plastic rings, etc., are provided on the handpiece to seal the gaps or the coil. These sealing devices increase the manufacturing effort involved in the handpiece and make it more complicated.

It is therefore an object to create a medical, in particular dental, handpiece, which does not have the aforementioned disadvantages and protects the coil of the handpiece in particular from soiling without requiring a plurality of additional sealing elements.

SUMMARY

In one embodiment, a medical or dental handpiece comprises an outer shell, a hollow shaft to accommodate a treatment tool, wherein the shaft is provided in the outer shell and can be driven to move, and a first coil for inductive coupling, in particular for inductive power and/or data exchange, with a memory unit of the treatment tool comprising a second coil, wherein the hollow shaft extends along a central axis and has an axial extent and a radial extent based on the central axis, and wherein the first coil is arranged within or beyond the axial extent of the hollow shaft and within the radial extent of the hollow shaft. This feature is met when at least a portion of the first coil is arranged within the radial extent of the hollow shaft, even if other parts of the coil are optionally situated outside of the radial extent of the hollow shaft.

Due to the arrangement of the coil within the radial extent of the hollow shaft, in particular at the end of the hollow shaft opposite the tool receptacle opening, the coil is protected from the soiling that occurs during treatment by the hollow shaft, by the tool accommodated in the hollow shaft and optionally by additional components arranged around the hollow shaft, such that no additional sealing devices for the coil need be provided on the handpiece.

The term handpiece comprises all straight or gun-shaped handpieces or handles, curved handpieces or handles, which are often referred to as contra-angle handpieces in the dental field, as well as parts of handpieces having a hollow shaft to receive a treatment tool, in particular a head section of a handpiece, which can be connected to detachable handle sections, for example. The term "handpiece" is also understood to include both cordless handpieces, in particular those with a replaceable or chargeable power source, and handpieces comprising a power supply line and a regulating unit, control unit and/or power supply unit connected thereto. This definition of handpiece relates to all the embodiments and text passages described in this application.

The hollow shaft is preferably part of a detachable, in particular form-fit or force-fit tool receptacle.

The memory unit of the treatment tool preferably comprises, in addition to the second coil, an electronic chip having a microprocessor and an electronically programmable memory designed either as a read-only memory or as a random-access memory. The inductive coupling of the two coils acting as antennas serves to supply power to the memory unit as well as for data exchange. This means that the electric power required for operation of the microprocessor and the memory in particular is transferred via the two coils to the memory unit of the treatment tool from the handpiece, which is connected by electric lines to a power source or comprises a power source (battery or accumulator). In addition, the two coils also serve as communication devices, in particular as antennas transmitting data in the form of electric signals uni- or bidirectionally. The data exchange between the two coils is preferably embodied as a modulated signal transmission, in particular in the high-frequency or radio-frequency range, wherein the memory unit comprises an RFID label comprising an RFID chip and a coil.

The treatment tool comprising the memory unit is designed, for example, as a tool that can be rotated, preferably for working on hard or soft tissue or for introducing an implant, in particular as a rotary drill or as a tool that can be brought to a reciprocating movement or to vibration. Accordingly, the hollow shaft holding the treatment tool is designed to be rotatable or movable back and forth or vibratable and/or mounted in the handpiece, and components, e.g., mechanical components such as gears or vibration generators are provided in the handpiece to provide the required working movement. The treatment tools comprise a working section and a shaft section for connecting the drive section to the handpiece, the memory unit preferably being arranged on the shaft section, in particular at least partially in the interior of the shaft section and/or on its free end.

The first coil is preferably arranged at the end of the hollow shaft facing the tool-holding/releasing device of the handpiece or is arranged adjacent to the end of the hollow shaft facing the tool-holding/releasing device of the handpiece. The first coil is especially preferably arranged in a cavity between the end of the hollow shaft facing the tool-holding/releasing device and a part of the tool-holding/releasing device, e.g., the operating element, in particular a pressure cover designed to be flat or curved or a cap of the tool-holding/releasing device designed to be flat or curved. The first coil is thus an especially great distance away from the tool receptacle opening and thus also away from the treatment site, so that it is especially well protected from the soiling that occurs during treatment.

Due to the immobile arrangement of the first coil with respect to the shaft, the data and power transfer to or from the coil is greatly simplified.

According to one embodiment, the first coil is arranged on a carrier, which is flat in particular, e.g., in the form of a plate or a disk, and is immovable or stationary with respect to the hollow shaft. This carrier allows a reliable means of fastening the first coil in the handpiece and additionally protects the first coil from soiling because of its flat shape. The carrier preferably comprises an electric insulating material, e.g., plastic, glass or ceramic, with which either the carrier is coated or of which the carrier is formed.

The carrier preferably has an opening around which the first coil is arranged and which is of such dimensions that it can be at least partially penetrated by the memory unit of the treatment tool, so that the first coil and the memory unit of the treatment tool, in particular its coil, can be arranged directly in one another or side-by-side next to one another. An especially good and reliable data and power transfer is thus achieved. The first coil and the opening of the carrier are arranged concentrically with the central axis of the hollow shaft in particular.

The carrier especially preferably also supports at least one line for power and/or data supply, this line being connected to the first coil, so that this at least one line is protected from mechanical stresses or breakage.

According to a preferred embodiment, the carrier has a side facing the tool receptacle opening of the handpiece and has a side facing away from the tool receptacle opening of the handpiece, wherein parts of the tool-holding/releasing device are arranged on both sides of the carrier. The first coil and/or the carrier are especially preferably surrounded or surroundable or penetrated or penetratable by at least a part of the tool-holding/releasing device, wherein the carrier has in particular a recess for being surrounded or penetrated by the at least one part of the tool-holding/releasing device. The first coil and/or the carrier is/are preferably surrounded or penetrated by the movable pressure cover or by a component connected to the movable pressure cover. Thus an especially space-saving integration of the carrier and the first coil into the handpiece and/or into the handpiece head can be achieved, so that the dimensions of the handpiece head, in particular its axial height based on the central axis of the hollow shaft, are as small as possible.

To permit an especially good and trouble-free power and data transfer, according to a preferred embodiment, the first coil is surrounded by an electric insulation layer, in particular at least one air gap around the first coil, an operating element comprising electrically nonconductive or electric insulating material or a carrier comprising electrically nonconductive or electric insulating material. The operating element or the carrier may be made entirely of the electrically nonconductive or electric insulating material, e.g., ceramic, glass or plastic, or it may be coated or sheathed with it.

For holding and releasing the treatment tool in the hollow shaft of the medical, in particular dental, handpiece it is provided with a tool-holding/releasing device. Essentially any tool-holding/releasing device may be used for the inventive handpiece as long as this tool-holding/releasing device does not interfere with the arrangement of the first coil within or beyond the axial extent of the hollow shaft and within the radial extent of the hollow shaft. However, according to a preferred embodiment, the handpiece comprises a tool-holding/releasing device, which is described in detail below and facilitates in particular the integration of the first coil into the handpiece and the function of the first coil or the overall data and power transfer unit, which comprises the memory unit of the treatment tool in addition to the first coil.

In addition, reference is made explicitly to the fact that this preferred tool-holding/releasing device is of course also implementable in a handpiece that does not have a first coil or is not designed or suitable for receiving a treatment tool having a memory unit or is not designed or suitable for data and power transfer, in particular an inductive data and power transfer, as described in this application. In other words, the preferred tool-holding/releasing device, which is described below, also constitutes a separate inventive aspect independent of handpieces with data transfer. The preferred tool-holding/releasing device may thus be part of any medical, in particular dental, handpiece.

The preferred tool-holding/releasing device comprises at least one shaped element which protrudes through a bore into the hollow shaft and projects through this bore into the hollow shaft, a movably arranged locking sleeve, which cooperates with the shaped element and an operating element for moving the locking sleeve. According to an embodiment, the locking sleeve is connected to a roller bearing for mounting the hollow shaft or is designed as an integral part of an inner raceway of this roller bearing, wherein the roller bearing is arranged displaceably in the handpiece for moving the locking sleeve. According to this embodiment, the operating element of the tool-holding/releasing device is designed so that it acts on the roller bearing, in particular on its outer raceway, for moving the locking sleeve, or it comes in contact with the roller bearing, in particular its outer raceway. One advantage of this tool-holding/releasing device is its extremely small, space-saving extent, in particular its small axial extent (based on the central axis of the hollow shaft for accommodating the treatment tool). Another advantage of this tool-holding/releasing device is that the operating element does not come in contact with any rotating part of the tool-holding/releasing device, neither during operation of the handpiece nor during the chucking or releasing operation of the tool, thereby preventing the operating element from heating up.

Another advantage of this tool-holding/releasing device is that a contact area between the operating element and additional components of the tool-holding/releasing device is arranged radially outside in the handpiece head (with respect to the central axis of the hollow shaft accommodating the treatment tool). According to a preferred embodiment, the contact area required for releasing the treatment tool from the tool-holding/releasing device is formed by the pressure cover, in particular by at least one contact element provided on the peripheral area of the pressure cover, and by the roller bearing for support of the hollow shaft, in particular by its outer ring. In this way, a cavity to receive components is created inside and/or beneath the operating element or pressure cover, in particular in their central area, in particular for receiving a memory unit, which was described above and will be described again below, or for a coil for power transfer and/or data transfer.

An important feature of the tool-holding/releasing device is thus the operating element, comprising a cap and at least one contact element. According to one embodiment, the at least one contact element it is arranged on or attached to or arises from the immediate outer edge of the cap or in the peripheral area of the cap of the operating element, in particular at a radial distance from the locking sleeve. According to another embodiment, the inner diameter of the ring-shaped contact element or the inside clearance of the contact element is greater than the outside diameter of the locking sleeve. To release the tool from the tool-holding/releasing device and/or to secure it in the tool-holding/releasing device, the at least one contact element cooperates with the locking sleeve, the at least one contact element being connected to the locking sleeve either directly or indirectly via additional components, e.g., a roller bearing for support of the hollow shaft of the tool-holding/releasing device. These features and the embodiments mentioned above contribute toward the fact that a cavity for accommodating components is formed inside and/or beneath the operating element or pressure cover, in particular in their central area, in particular to receive the aforementioned coil or memory unit.

According to one embodiment, the tool-holding/releasing device comprises a cage in which the roller bearing is displaceably accommodated and in which a spring element prestressing the roller bearing is preferably accommodated. Preferably at least one spring element, in particular a spring arm, which prestresses the operating element, is provided on the cage, in particular as an integral component of a cage wall. Thus an especially compact and easy-to-install cartridge-type unit is created in an advantageous manner.

Another advantageous feature of the tool-holding/releasing device is that both the axial fixation of the treatment tool in the tool-holding/releasing device and the transfer of torsional moment to the treatment tool are accomplished by a single or joint holding and transfer unit. The holding and transfer unit comprises in particular the at least one shaped element protruding into the hollow shaft, in particular a shaped element having a spherical design. This makes it possible to design the hollow shaft as a hollow shaft having a cylindrical internal bore with a constant inside diameter over its entire length or with a continuous cylindrical inside wall, which is penetrated only by the at least one opening for the shaped element. Accordingly, the design of the tool shaft, in particular that section of the tool shaft accommodated in the hollow shaft, is continuously cylindrical except for the ring groove to receive the shape element, and has a constant outside diameter. The hollow shaft thus forms a continuous cylindrical guide or tool mount or a continuous cylindrical tool seat for the treatment tool.

Another inventive aspect relates to a medical, in particular dental, handpiece with a memory unit for storage of operating data and/or identification data of the handpiece, to a medical, in particular dental, treatment device having such a handpiece and a method for transmission of power and/or operating data and/or identification data with such a handpiece or such a treatment device. This handpiece also represents in particular a separate, independent inventive aspect. This means that according to a preferred embodiment, this handpiece has an inductive data and power transfer unit for data and/or power exchange with a memory unit of a treatment tool, in particular being equipped with an inductive data and power transfer unit for data and/or power exchange with a memory unit of a treatment tool such as that described in this document. According to an alternative embodiment, however, this handpiece does not have a data and power transfer unit for data and/or power exchange with a memory unit of a treatment tool. In addition, according to one embodiment, this handpiece has a tool-holding/releasing device such as that described in this document; alternatively, it has any other tool-holding/releasing device.

The memory unit of the handpiece has in particular a memory element for storage of operating data and/or identification data of the handpiece, a first coil which is provided on the handpiece and is connected to the memory element, and preferably a read and/or write device connected to the memory element for reading out of and/or writing to the memory element operational and/or identification data, wherein the power supply for the memory unit and/or the operational and/or identification data is/are optionally inductively transferable via the first coil provided on the handpiece or in a hardwired process by at least one optical or electric line connecting the memory unit to the coupling device. In particular the data transfer may be either unidirectional or bidirectional.

One advantage of this handpiece consists of, among other things, the fact that through the optional inductive or hardwired power and/or data transfer, the possibility of transmitting power or data to the handpiece or receiving them from the handpiece is created, regardless of whether or not the handpiece is mechanically connectable to the power source or to the data transmitter or receiver. Thus, for example, the handpiece may be placed in a cleaning device, in particular a disinfector or sterilizer, for cleaning it without being mechanically coupled to the cleaning device. For verification of the cleaning, information is stored inductively in the memory element, e.g., the fact that the handpiece has been cleaned or which type of cleaning has been performed or how often it has been cleaned on the whole. To do so, the cleaning device has a corresponding inductive transmission unit, which is provided with or connected to a power source, an antenna, designed in particular as a coil, and a data source, so that power and data in the form of electric signals can be transferred from the cleaning device to the handpiece. The power and/or data transfer is preferably designed as a high-frequency signal transmission between the two coils, in particular in the radio-frequency range, the memory unit comprising an RFID chip or an RFID label. If, after being cleaned, the handpiece is connected by means of a mechanical coupling, e.g., a plug coupling or a rotary plug coupling, to a control and/or power supply unit comprising the corresponding lines for the power and/or data transfer, then the data regarding cleaning stored in the memory element are read out by the control circuit or a microprocessor of the control and/or power supply unit in a hardwired operation. According to a preferred embodiment, the control and/or power supply unit allows operation of the handpiece only when the data from the memory element of the handpiece indicate that the handpiece has been cleaned.

If the control and/or power supply unit does not have any lines or contacts to enable hardwired access to the data in the memory unit or to facilitate a power supply to the memory unit, then according to an alternative embodiment, these data may be read out of the memory unit via a separate reading and/or sending device. The reading and/or sending device is connected via lines to the control and/or power supply unit and forwards the readout data to the control and/or power supply unit, e.g., for processing or for operation of the handpiece. The reading and/or sending device is inductively couplable to the memory unit of the handpiece for the purpose of power and/or data transfer and is provided with or connected to a power source, an antenna, designed as a coil in particular, and a reading and/or sending unit.

It is clear from the above description that the power and/or data transfer between the memory unit of the handpiece and the control and/or power supply unit may optionally take place by induction, in particular via a reading and/or sending device, which is an integral part of the control and/or power supply unit or is a separate component which is connected to the control and/or power supply unit via lines, or the power and/or data may be transferred in a hardwired process, optionally via intermediate pieces such as a motor, a coupling, an adapter, etc. This advantageously creates a universal handpiece, which can exchange data and/or power with a new control and/or power supply unit, which is provided with corresponding lines for the hardwired power and/or data transfer as well as with an older control and/or power supply unit, which does not have such lines but is connected to a reading and/or sending device, which is inductively couplable to the handpiece. It is of course also possible to perform the power and/or data transfer between the handpiece and the reading and/or sending device in a hardwired operation.

In addition to the coil acting as an antenna, the memory unit of the handpiece comprises an electronically programmable memory, which is designed either as a ROM (read-only memory) or as a RAM (random-access memory), and a chip or microprocessor, which also forms the read and/or write device for reading out of and/or writing to the memory element operational and/or identification data. The inductive data transfer is preferably designed as a high-frequency signal transmission, in particular in the radio-frequency range, wherein the memory unit of the handpiece comprises an RFID chip or an RFID label.

According to one embodiment, the at least one optical or electric line of the handpiece connects the memory unit to the coupling device and ends in at least one contact on the coupling device, so that the power and/or the operational and/or identification data is/are transferable over the coupling device between the memory unit and the control and/or power supply unit. For example, the coupling device is designed as part of a plug, screw, rotary or rotary-plug coupling having the corresponding mating coupling elements. The at least one optical or electric line or the at least one contact ends either directly on the outer shell or on the exterior end face of the coupling device or is situated in a protected manner in a receptacle or in a setback, in particular in a coupling tube into which a line, a contact or a part of a mating coupling element engages.

According to one embodiment, the entire memory unit is arranged on a single carrier element, in particular a circuit board. Thus, especially good protection of the memory unit from soiling and moisture can be achieved, because the entire memory unit as well as the lines connecting the individual components of the memory unit can be enclosed in a shared protective device, e.g., a housing made of metal or plastic, a coating of lacquer or a cast material. According to an alternative embodiment, one or more parts of the memory unit, in particular the first coil provided on the handpiece and the memory element, are arranged on different carrier elements, which are connected to one another by electric lines. Thus specific requirements of the respective parts of the memory unit may be taken into account especially well, e.g., the fact that the first coil is arranged in a position on the handpiece, where the most interference-free inductive power and/or data transfer is possible, e.g., directly on or directly beneath the outer shell or in the head part of the handpiece.

To permit especially good and interference-free power and data transfer, according to a preferred embodiment, at least one section of the outer shell, in particular the section of the outer shell, which surrounds the first coil provided on the handpiece, comprises a magnetically nonconductive and electrically nonconductive material, in particular plastic, glass or ceramic. This section of the outer shell is formed, for example, by the pressure cover of the tool-releasing device of the handpiece or by a cylindrical or arc-shaped part of the neck section of the handpiece.

According to one embodiment, the handpiece has a head section accommodating the connecting device for the treatment tool, a neck section connected to the head section and a handle section arranged preferably at an angle to the neck section and connected to the neck section, wherein the first coil provided on the handpiece is arranged in the head section or in the neck section. Handling of the handpiece that is advantageous in particular for the inductive power and/or data transfer is thus achieved, because the user can hold the handpiece in his hand as he also holds it for the treatment, so that the user need not change his grip on the handpiece between the inductive power and/or data transfer and the start of use of the handpiece.

According to a preferred embodiment, the handpiece is part of an inductive power and data transfer unit for transmitting power and data between a control and/or power supply unit, the handpiece and at least one treatment tool drivable by the handpiece. There is a power and/or data transfer not only between the handpiece and the control and/or power supply unit but also between the treatment tool and the control and/or power supply unit, wherein preferably at least a part of the power and/or data transfer between the treatment tool and the control and/or power supply unit takes place via or through the handpiece.

According to an embodiment, a second coil is provided on the handpiece for this purpose, this coil being arranged in the head section of the handpiece, in particular at the connecting device for the treatment tool, such that it can be inductively coupled to a coil of a memory unit of the treatment tool for power and/or data transfer. This second coil thus supplies a memory unit of the treatment tool inductively with power and inductively transmits data from or to the memory unit of the treatment tool. The memory unit of the treatment tool comprises a coil, preferably an electronic chip with a microprocessor and an electronically programmable memory, which is designed either as a read-only memory or as a random-access memory. This inductive power and/or data transfer preferably has the same design, the same arrangement, the same features and/or the same functioning as that described in this document for an inductive power and/or data transfer between a memory unit of a treatment tool and a coil in a handpiece.

The power and/or data transfer to or from the second coil provided in the handpiece is accomplished by a hardwired method, wherein the second coil is therefore connected to the coupling device either directly via at least one optical or electric line or via the memory unit for storage of operational and/or identification data of the handpiece and at least one optical or electric line. If the data of the treatment tool are transferred over the memory unit for storage of operational and/or identification data of the handpiece, then this memory unit preferably serves as interim storage for the data of the treatment tool. Alternatively, the power supply for the memory unit of the treatment tool is transferred inductively directly between an external coil connected to a power source and the coil of the memory unit of the treatment tool.

According to an alternative preferred embodiment of the inductive power and data transfer unit for transferring power and data between a control and/or power supply unit, the handpiece and at least one treatment tool drivable by the handpiece, the first coil provided on the handpiece is arranged at the connecting device for the treatment tool such that it is inductively couplable to a coil of a memory unit of the treatment tool for power and/or data transfer. In other words, only one coil is provided on the handpiece, wherein the power and/or data transfer between the memory unit of the tool and the control and/or power supply unit takes place by means of this coil, and the power and/or data transfer between the memory unit of the handpiece and the control and/or power supply unit takes place by means of this coil. This advantageously eliminates the second coil being provided on the handpiece and all the components for power and/or data transfer cooperating with the second coil.

This first coil provided on the handpiece is connected to the memory element of the memory unit for storage of operational and/or identification data of the handpiece, as already described above, so that power and/or data is/are inductively transferable between the memory unit of the handpiece and a reading and/or sending device. The first coil and the first memory element are thus arranged either on a common carrier element or next to one another or they are arranged with a distance between them in the handpiece and are connected to one another by electric lines.

According to this alternative embodiment, the first coil provided on the handpiece also serves at least for inductive data transfer between the memory unit of the treatment tool and the control and/or power supply unit. The data of the treatment tool are preferably transferred via the first coil to the memory unit for storage of operational and/or identification data of the handpiece and are stored temporarily there, so that the memory unit of the handpiece forms a temporary storage for the data of the treatment tool. Next the data of the treatment tool are inductively transferred from the intermediate storage to a read and/or control unit via the first coil or the data are transferred inductively from the intermediate memory to the memory unit of the treatment tool via the first coil. It is of course also possible to transfer the data of the treatment tool by wire between the interim memory and the coupling device.

Power is supplied to the memory unit of the treatment tool via direct inductive coupling, either between the coil of the reading and/or sending device and the coil of the memory unit of the treatment tool, or in a hardwired operation, likewise via the first coil provided on the handpiece, which is or can be connected directly to a power source or via the memory unit of the handpiece for this purpose. The memory unit of the handpiece and the first coil are preferably supplied with power via shared electric lines.

The connecting device preferably has a releasable, form-fit or force-fit tool receptacle into which the treatment tool can be inserted via a tool receptacle opening. The connecting device is itself connected to a drive unit, which comprises, for example, one or more shafts, toothed wheels, gears, an air motor or an electric motor, a fluid-operated rotor and/or fluid lines.

To achieve the highest-quality power and/or data transfer with the least possible interference, according to one embodiment the first coil provided on the handpiece or the second coil provided on the handpiece surround the connecting device for the treatment tool at least partially, or they are arranged next to the end of the connecting device facing away from the tool receptacle opening. For the same reason, according to another embodiment, the first coil or the second coil is surrounded by an electric insulation layer, which in particular has at least one air gap around the first or second coil, an operating element of the tool-releasing device comprising electrically nonconductive material or a carrier element comprising electrically nonconductive material.

According to another embodiment, to minimize the risk of soiling of the first coil provided on the handpiece or of the second coil provided on the handpiece due to particles penetrating into the handpiece, the first coil or second coil is arranged within or beyond the axial extent of the connecting device and within the radial extent of the connecting device. In particular, the first coil or the second coil is arranged in a cavity between the end of the connecting device facing away from the tool receptacle opening and an operating element of the tool-releasing device, in particular the pressure cover.

The medical, in particular dental, treatment device comprises a medical, in particular dental, handpiece described above and a reading and/or sending device having a coil provided on the reading and/or sending device, which can be coupled inductively for the purpose of power and/or data transfer to the first coil provided on the handpiece and/or to the second coil provided on the handpiece and/or to a coil of a memory unit of the treatment tool. The reading and/or sending device is preferably operatively connected to the control and/or power supply unit or is designed as an integral part of the control and/or power supply unit.

In a method for transfer of power and/or operational and/or identification data with a medical, in particular dental, handpiece as described above or with a medical, in particular dental, treatment device as described above, the transfer of power and/or operational and/or identification data optionally takes place inductively via the first coil provided on the handpiece or in a hardwired operation via at least one optical or electric line connected to the memory unit. The first coil provided on the handpiece or the second coil provided on the handpiece is preferably arranged on the connecting device for the treatment tool in such a way as to permit inductive power and/or data transfer with the coil of the memory unit of the treatment tool.

The medical or dental handpiece, the medical or dental treatment device and the method for transferring power and/or operational and/or identification data may have one or more of the following features:

1. Medical, in particular dental, handpiece comprising an outer shell, a connecting device for connecting a treatment tool which is arranged in the outer shell and can be induced to a driving motion, a coupling device for connecting the handpiece with a control and/or power supply unit, and a memory unit, which is connected by at least one optical or electric line to the coupling device, wherein
   the memory unit comprises a memory element for storage of operational and/or identification data of the handpiece and preferably a read and/or write device connected to the memory element for reading out and/or writing to the memory element operational and/or identification data, and wherein a first coil is provided on the handpiece and connected to the memory unit, so that the power supply for the memory unit and/or the operational and/or identification data is/are inductively transferable via the first coil provided on the handpiece or via the at least one optical or electric line in a hardwired process.
2. Medical, in particular dental, handpiece according to point 1, wherein the at least one optical or electric line or at least one contact of the at least one optical or electric line end(s) in an end face of the coupling device or in a coupling tube of the coupling device.
3. Medical, in particular dental, handpiece according to point 1 or 2, wherein the entire memory unit is arranged on a single carrier element, in particular a circuit board, or wherein one or more parts of the memory unit, in particular the first coil provided on the handpiece and the memory element are arranged on different carrier elements, which are interconnected via electric lines.

4. Medical, in particular dental, handpiece according to any one of the preceding points, wherein
at least one section of the outer shell, in particular the section of the outer shell surrounding the first coil provided on the handpiece comprises a magnetically nonconductive and electrically nonconductive material, in particular plastic, glass or ceramic.

5. Medical, in particular dental, handpiece according to any one of the preceding points, wherein
the handpiece has a head section receiving the connecting device for the treatment tool, a neck section connected to the head section and a handle section connected to the neck section, and preferably arranged at an angle to the neck section, wherein the first coil provided on the handpiece is arranged in the head section or in the neck section.

6. Medical, in particular dental, handpiece according to any one of the preceding points, wherein
the first coil provided on a handpiece is arranged at the connecting device for the treatment tool such that it is inductively couplable to a coil of a memory unit of the treatment tool for power and/or data transfer.

7. Medical, in particular dental, handpiece according to any one of points 1-5, comprising
a second coil provided on the handpiece and arranged at the connecting device for the treatment tool in such a way that it is inductively couplable to a coil of a memory unit of the treatment tool for power and/or data transfer.

8. Medical, in particular dental, handpiece according to any one of points 6 or 7, wherein
the first coil provided on the handpiece or the second coil provided on the handpiece surrounds at least partially the connecting device for the treatment tool or is arranged at the end of the connecting device facing away from the tool receptacle opening.

9. Medical, in particular dental, handpiece according to any one of points 6-8, wherein the connecting device extends along a central axis and has an axial extent and a radial extent, based on the central axis, and wherein the first coil provided on the handpiece or the second coil provided on the handpiece is arranged within or beyond the axial extent of the connecting device and within the radial extent of the connecting device.

10. Medical, in particular dental, handpiece according to any one of points 6-9, wherein
the first coil provided on the handpiece or the second coil provided on the handpiece is arranged in a cavity between the end of the connecting device facing away from the tool receptacle opening and an operating element of the tool-releasing device, in particular the pressure cover.

11. Medical, in particular dental, handpiece according to any one of the preceding points, wherein
the first coil provided on the handpiece or the second coil provided on the handpiece is surrounded by an electric insulation layer, which comprises in particular at least one air gap around the first or second coil, an operating element of the tool-releasing device comprising nonconductive material or a carrier element comprising nonconductive material.

12. Medical, in particular dental, treatment device comprising a medical, in particular dental, handpiece according to any one of the preceding points and a reading and/or sending device having a coil provided on the reading and/or sending device, which can be coupled inductively to the first coil provided on the handpiece and/or to the second coil provided on the handpiece and/or to a coil of a memory unit of the treatment tool for power and/or data transfer.

13. Medical, in particular dental, treatment device according to point 12, wherein the reading and/or sending device is operatively connected to the control and/or power supply unit or is designed as an integral part of the control and/or power supply unit.

14. Method for transmitting power and/or operational and/or identification data with a medical, in particular dental, handpiece or with a medical, in particular dental, treatment device according to any one of the preceding points, wherein
power and/or operational and/or identification data is optionally transferred inductively via the first coil provided on the handpiece or in a hardwired process via at least one optical or electric line connected to the memory unit.

15. Method for transmitting power and/or operational and/or identification data according to point 14, wherein
the first coil provided on the handpiece or the second coil provided on the handpiece is arranged at the connecting device for the treatment tool in such a way that there is an inductive power and/or data transfer with the coil of the memory unit of the treatment tool.

In addition, any of the features already described above, wherein a medical, in particular dental, handpiece comprises only a single coil by means of which the power and/or data transfer between the memory unit of the tool and the control and/or power supply unit takes place and by means of which the power and/or data transfer between the memory unit of the handpiece and the control and/or power supply unit takes place, also constitutes an independent inventive aspect. A handpiece having this feature may therefore be combined with embodiments of other handpieces described in the present application, but it may also have none of the other embodiments described in this application.

The medical, in particular dental, handpiece may have one or more of the following features:

1. Medical, in particular dental, handpiece comprising an outer shell, a connecting device for connection of a treatment tool arranged in the outer shell and inducible to a driving movement, a coupling device for connection of the handpiece to a control and/or power supply unit, and a first coil arranged at the connecting device, said first coil being configured for inductive coupling, in particular for inductive power and/or data exchange, with a memory unit of the treatment tool comprising a second coil for storage of tool-based data, wherein
the first coil is electrically connected by electric lines to a memory element provided in the handpiece for storage of handpiece-related data, so that the tool-related data and the handpiece-related data are transferable between the first coil and a reading and/or sending device inductively couplable to the first coil.

2. Medical, in particular dental, handpiece according to point 1, wherein the memory element provided in the handpiece comprises a writable memory in which the tool-related data can be stored.

3. Medical, in particular dental, handpiece according to point 1 or 2, wherein the first coil and the memory element provided in the handpiece are arranged side-by-side or at a distance from one another or on a single carrier element, in particular a circuit board, or on different carrier elements.

4. Medical, in particular dental, handpiece according to any one of the preceding points, comprising
   a hardwired power supply for the memory element provided in the handpiece and for the first coil, in particular through shared electric lines extending from the coupling device.

5. Medical, in particular dental, handpiece according to any one of the preceding points, wherein
   the first coil at least partially surrounds the connecting device for the treatment tool or is arranged at the end of the connecting device facing away from the tool receptacle opening.

6. Medical, in particular dental, handpiece according to any one of the preceding points, wherein
   the connecting device extends along a central axis and has an axial extent and a radial extent, based on the central axis, and wherein the first coil is arranged within or beyond the axial extent of the connecting device and within the radial extent of the connecting device.

7. Medical, in particular dental, handpiece according to any one of the preceding points, wherein
   the first coil is arranged in a cavity between the end of the connecting device facing away from the tool receptacle opening and an operating element of the tool-releasing device, in particular the pressure cover.

8. Medical, in particular dental, handpiece according to any one of the preceding points, wherein
   the first coil is surrounded by an electric insulation layer, which comprises in particular at least one air gap around the first coil, an operating element of the tool-releasing device comprising electrically nonconductive material or a carrier element comprising electrically nonconductive material.

9. Medical, in particular dental, treatment device comprising a medical, in particular dental, handpiece according to any one of the preceding points and a reading and/or sending device with a coil provided on the reading and/or sending device, which is couplable inductively with the first coil provided on the handpiece for power and/or data transfer.

10. Medical, in particular dental, treatment device according to point 9, comprising
    a treatment tool with a memory unit comprising a second coil for storage of tool-related data.

11. Medical, in particular dental, treatment device according to point 9 or 10, wherein
    the reading and/or sending device is operatively connected to a control and/or supply unit or is designed as an integral part of a control and/or power supply unit.

12. Medical, in particular dental, treatment device according to any one of points 9-11, comprising
    a control device for optional or sequential transmission of the tool-related data and the handpiece-related data.

13. Method for inductive data transfer having a medical, in particular dental, handpiece or having a medical, in particular dental, treatment device, wherein
    the tool-related data and the handpiece-related data are transferred between the first coil and a reading and/or sending device inductively couplable with the first coil.

14. Method for inductive data transfer according to point 13, wherein the memory element provided in the handpiece comprises a writable memory in which the tool-related data are stored.

15. Method for inductive data transfer according to point 14, wherein the control device transmits the tool-related data and the handpiece-related data optionally or sequentially.

One advantage of the handpiece having a coil for transmission of the tool-related data and the handpiece-related data is in particular that it eliminates the second coil plus all the components for power and/or data transfer that cooperate with the second coil.

According to one embodiment, the memory element provided in the handpiece comprises a writable memory in which tool-related data can be stored. Thus, an especially efficient method for data transfer can be implemented, in which the user must bring the handpiece into proximity to the reading and/or sending device only once to transmit the tool-related data and the handpiece-related data.

If this method includes, for example, a reading operation, in which tool-related data are read out of the memory unit of the treatment tool, then the method preferably comprises the following steps: First, the first coil and the memory element provided in the handpiece and having the writable memory are provided with power, the power supply in particular being accomplished via the coupling device of the handpiece in a hardwired method. Based on the inductive coupling of the first coil with the memory unit of the treatment tool comprising a second coil, the memory unit is also supplied with power. In the next step, tool-related operational and/or identification data are read out of the memory using a microprocessor of the memory unit and are transferred inductively to the first coil in the handpiece. The data are sent from the first coil to the writable memory of the memory element of the handpiece in a hardwired method and stored there. Next, the handpiece and the reading and/or sending device are brought into proximity to one another, so that an inductive coupling is achieved between the first coil of the handpiece and another coil in the reading and/or sending device. As soon as this inductive coupling is maintained, the tool-related data are transferred in a hardwired method to the first coil in the handpiece and then transferred inductively from the first coil to the coil of the reading and/or sending device. During the inductive coupling between the first coil of the handpiece and the additional coil in the reading and/or sending device, handpiece-related data from the memory element of the handpiece are preferably also transferred inductively in the same way via the first coil to the reading and/or transmitting device, in particular with the transmission of the handpiece-related and tool-related data occurring sequentially. It is of course also possible to optionally transmit only the tool-related or handpiece-related data stored in the memory element of the handpiece to the reading and/or sending device. The data received by the reading and/or sending device are stored and/or processed by it and/or forwarded to an evaluation unit, in particular to the control and/or supply unit for the handpiece.

If data are written to the memory unit of the treatment tool, then the entire process takes place in the opposite order, i.e., after the power supply to the memory element with the writable memory provided in the handpiece and the first coil, then the tool-related data are first transferred inductively to the first coil of the handpiece, stored temporarily in the memory element of the handpiece and then transferred inductively via the first coil to the memory element of the tool and stored there.

According to an embodiment, the handpiece has a hardwired power supply of the memory element provided in the handpiece and the first coil, formed in particular by shared electric lines extending from the coupling device. Thus in an advantageous manner, a data transfer between the memory unit of the treatment tool and the memory element of the handpiece is possible without having to bring the handpiece into the vicinity of the reading and/or sending device for this purpose in order to obtain power from it inductively.

These and other embodiments will now be explained below on the basis of several preferred embodiments and with reference to the accompanying drawings:

DETAILED DESCRIPTION

Figure 1:
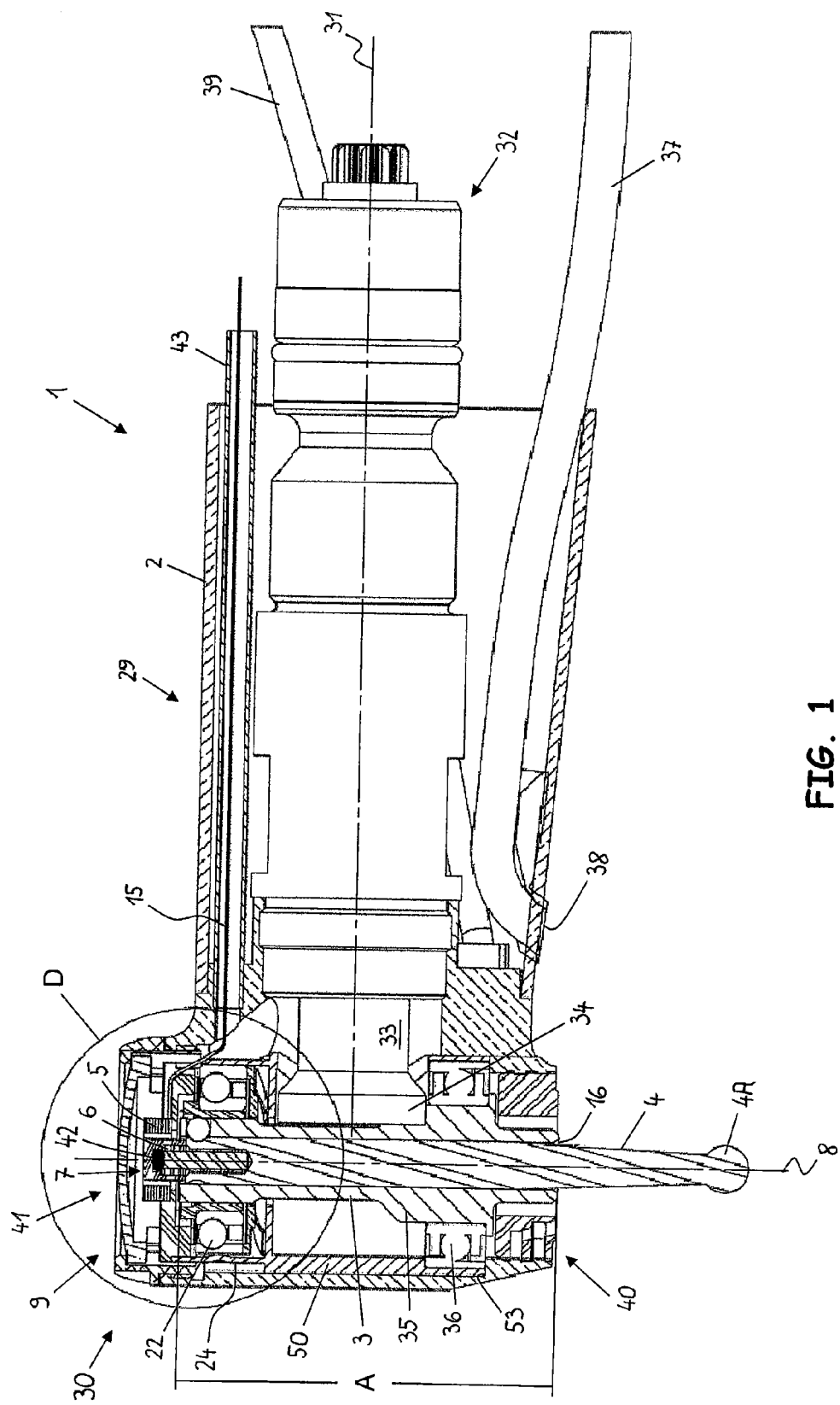
FIG. 1 shows a sectional diagram of a first embodiment of a medical or dental handpiece having a tool-holding/releasing device and an inductive data and power transfer unit comprising a first coil in the handpiece and a memory unit attached to a treatment tool with a data memory and a second coil connected to the data memory.

FIG. 1 shows a medical or dental handpiece, having an outer shell 2. The handpiece 1 consists of a handle section 29 and a head part 30. A tool receptacle opening 16 for receiving a treatment tool 4 is provided laterally on the head part 30, so that the tool 4 is arranged at an angle to the longitudinal axis 31 of the handle section 29. In the illustrated example, the tool 4 is designed as a dental drill that is rotatable.

A drive train or driving means 32, in particular one or more drive shafts 33, which are or can be connected to a motor, are provided in the interior of the hollow elongated handle section 29. The drive shaft 33 has a gearwheel 34 on its end facing the head part 30, said gearwheel 34 meshing with another gearwheel or pinion 35 in the head part 30. The gearwheel 35 is connected to a hollow shaft 3 or is designed as part of the hollow shaft 3. The hollow shaft 3 serves to receive the treatment tool 4, so that the drive movement of the motor is transferable to the treatment tool 4 by way of the drive train or driving means 32 comprising the shaft 33, the gearwheels 34, 35 and the hollow shaft 3.

The hollow shaft 3 is mounted rotatably in the head part 30 of the handpiece 1 by two roller bearings, in particular ball bearings 22, 36. The hollow shaft 3 has an axis of rotation or central axis 8, an axial extent A and a radial extent R (see FIGS. 2 and 3). The hollow shaft 3 is made of metal, for example, in particular steel, but according to one embodiment, it may also be manufactured from an electrically nonconductive material, in particular a ceramic, so as not to influence the inductive power or data transfer.

In addition, one or more media lines, e.g., an optical conductor 37, in particular a glass fiber rod, which conducts radiation of a radiation source to a light-emitting window 38, and one or more fluid lines 39, in particular for conducting treatment fluids such as compressed air and/or water, are provided in the handle section 29. The at least one fluid line 39 is connected to one or more fluid sources and to a fluid-dispensing device 40, comprising, for example, one or more fluid-dispensing openings, a mixing chamber or a spray plate. The fluid-dispensing device 40 is arranged around the tool receptacle opening 16.

In addition, a tool-holding/releasing device 9 for securing the tool 4 in the hollow shaft 3 and for releasing the tool 4 out of the hollow shaft 3 and a first coil 5 are arranged in the head part 30 of the handpiece 1. The entire tool-holding/releasing device 9 is on the end of the hollow shaft 3 facing away from the tool receptacle opening 16. The first coil 5, which is also arranged at or adjacent the end of the hollow shaft 3 facing away from the tool receptacle opening 16 is accommodated in a receptacle or in a cavity 11 (see FIGS. 2 and 3) within the tool-holding/releasing device 9 or in a cavity 11 formed by the tool-holding/releasing device 9. The volume of the cavity 11 is preferably designed to be larger than the volume or the outside circumference of the first coil 5, so that the cavity 11, in particular that part of the cavity 11 which is filled with air, is also part of an electric insulation layer that surrounds the first coil 5.

The first coil 5 is part of a data and power transfer unit 41, which further comprises a memory unit 7 provided on the tool 4. The memory unit 7 has a second coil 6 and a memory 42, the memory 42 being designed either as a read-only memory (ROM) or as a read-and-write, i.e., random-access memory (RAM). The two coils 5, 6 are inductively coupled to one another, so that power and/or data may be transferred between the coils 5, 6. To do so, the first coil 5 is or can be connected to a power source arranged inside or outside the handpiece 1 via one or more electric lines 15, e.g., two electric lines. The electric power made available by the power supply is transferred inductively from the first coil 5 to the second coil 6 and then further to the memory 42. Through this power supply, the memory 42 can be activated and the memory data, e.g., identification data or operating data of the tool 4 is read out from the memory 42 and/or memory data, e.g., data about the operating time, the cleanliness or sterility status or about the wear on the tool 4 may be written to the memory 42. The memory data are also transferred inductively via the two coils 5, 6, which thus also serve as antennas and guarantee data transfer, preferably high-frequency data transfer, in particular in the radio-frequency range. Accordingly, the memory 42 preferably comprises an RFID chip or an RFID label. Conducting the memory data from the memory 42 or optionally to the memory 42 likewise takes place over the at least two electric lines 15.

The two electric lines 15 run in the interior of the handpiece 1 and are electrically insulated from metallic components of the handpiece 1, in particular from the outer shell 2, by insulation means, e.g., a plastic shell. Furthermore the lines 15 are surrounded by a plastic or metal tube 43, which serves to shield the lines 15 from external interfering fields, e.g., from magnetic fields or electric fields originating from an electric motor driving the tool 4 in particular.

For further processing of the memory data obtained from the memory 42 and/or for delivery of memory data to the memory 42, a control unit, in particular a microprocessor, which is connected to the memory 42 by the at least two electric lines 15, is provided inside or outside the handpiece 1. The control unit preferably receives identification data from the memory 42 identifying the tool 4 inserted into the hollow shaft 3 of the handpiece 1 and connected to the memory 42 and serving to control the motor driving the handpiece 1 or the coolant supply. For example, the torque or rotational speed of the motor or the amount of coolant supplied to the tool 4 is limited in this way to maximum levels, which correspond to the properties of the tool or comply with the requirements of the medical treatment which can be performed with the tool 4. According to this especially preferred embodiment, the control unit together with the electric lines 15 and the data and power transfer unit 41 thus form a tool recognition device.

Figure 2:
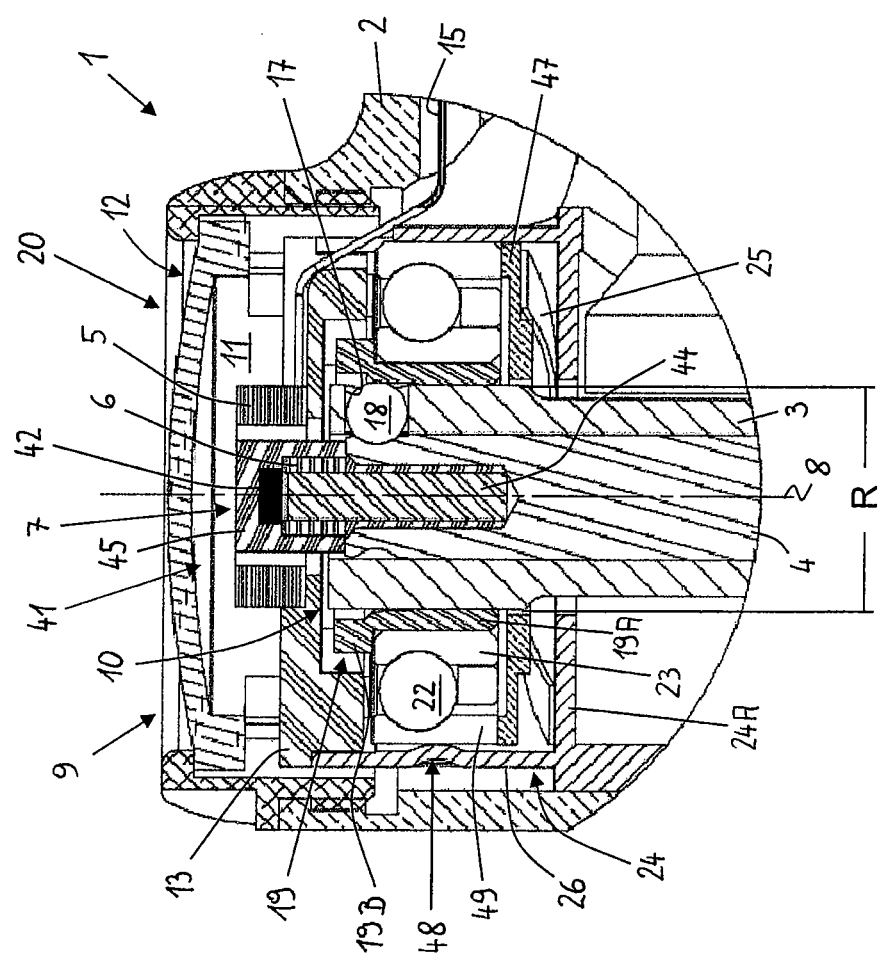
FIG. 2 shows the detail labeled as "D" of the sectional diagram of FIG. 1 with the inductive data and power transfer unit and the tool-holding/releasing device for attaching the treatment tool to the handpiece and releasing the treatment tool from the handpiece.
Figure 3:
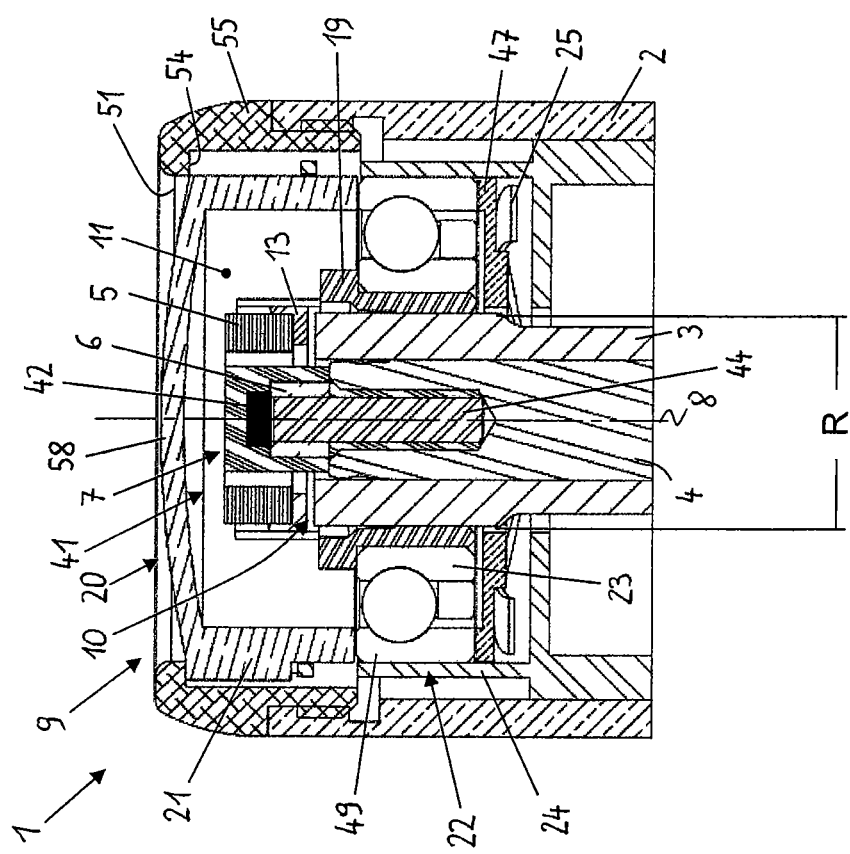
FIG. 3 shows another sectional diagram through the head part of the handpiece of FIG. 1 with the inductive data and power transfer unit and the tool-holding/releasing device, whereby the sectional plane is normal to the sectional plane of FIG. 1.

FIGS. 2 and 3 in particular show the detailed design of the data and power transfer unit 41. The memory unit 7 connected to the tool 4, preferably undetachably, comprises the second coil 6, the memory 42 and a ferrite core 44, in particular in a rod shape. The memory unit 7 is arranged at and/or on the end of the tool 4 opposite the treatment section 4A (see FIG. 1), wherein parts of the memory unit 7, in particular the ferrite core 44, are countersunk in the tool shaft and/or in a receptacle of the tool shaft. Alternatively, the entire memory unit 7 is placed on the end of the tool shaft without parts of the memory unit 7 protruding into the tool shaft. Fastening means 45, e.g., a nonconductive insulating material, preferably a cast resin, in particular epoxy resin, fasten the memory unit 7 on the tool 4. The electronic memory 42 is preferably part of an electronic chip, which additionally comprises a microprocessor or circuit, e.g., for reading the data out of the memory 42, for supplying power to the memory 42 or optionally for writing data to the memory 42.

The data and power transfer unit 41 additionally comprises the first coil 5 arranged immovably in the handpiece 1 with respect to the hollow shaft 3. The first coil 5 is supported on a flat, in particular plate-shaped or disk-shaped, carrier 13, which is arranged immovably in the handpiece 1 and/or immovably with respect to the hollow shaft 3. The carrier 13 has an opening 14 (see FIG. 5) about which the first coil 5 is arranged and which is of such dimensions that it can be penetrated at least partially by the memory unit 7 of the treatment tool 4, so that the first coil 5 and the memory unit 7 of the treatment tool 4, in particular its second coil 6, can be arranged inside of one another, and an inductive power and/or data transfer between the two coils 5, 6 is possible. One or more setbacks or recesses 46A, 46B on the carrier 13 serve to receive or support the first coil 5 and the electric lines 15 connected to the first coil 5. The carrier 13, which is part of an electric insulation layer surrounding the first coil 5 preferably comprises an electric insulating material, in particular plastic, glass or ceramic.

The first coil 5 is arranged at or adjacent the end 10 of the hollow shaft 3 facing the tool-holding/releasing device 9 of the handpiece 1 outside of the axial extent (A) and within the radial extent (R) of the hollow shaft 3. The opening 14 of the carrier 13 and the first coil 5 are arranged concentrically with the central axis 8 of the hollow shaft 3.

In addition, FIGS. 2 and 3 show the detailed design of the tool-holding/releasing device 9. The tool holding/releasing device 9 is arranged at the end 10 of the hollow shaft 3 opposite the tool receptacle opening 16 and/or surrounds this end 10. The tool holding/releasing device 9 comprises, among other things, a shaped element 18, which projects through a bore 17 in the hollow shaft 3 and protrudes through the bore 17 into the interior of the hollow shaft 3, a movably arranged locking sleeve 19 cooperating with the shaped element 18 and an operating element 20 for moving the locking sleeve 19. The shaped element 18 is designed as a sphere, hemisphere, ellipsoid or cylinder, for example. To achieve a uniform and secure chucking of the tool 4 in the hollow shaft 3, multiple shape elements 18, e.g., three shape elements 18, are preferably arranged around the hollow shaft 3, in particular uniformly.

The locking sleeve 19 surrounds the hollow shaft 3 and is axially displaceable along the central axis 8 of the hollow shaft 3. The locking sleeve 19 comprises a first section 19A with a first inside diameter and a second section 19B with a second larger inside diameter, the second section 19B being a distance away from the outer jacket of the hollow shaft 3. The two sections 19A, 19B are joined together by a short conical section. If the locking sleeve 19 is displaced into a position, in which the first section 19A comes in contact with the shaped element 18, as shown in FIG. 2, and presses it into the bore 17 so far that a part of the shaped element 18 protrudes into the interior of the hollow shaft 3, then the shaped element 18 contacts the tool 4 inserted into the hollow shaft 3, in particular one or more recesses on the tool shaft, so that the tool 4 is axially attached in the hollow shaft 3 and is secured for transferring the torque to the tool 4. If the locking sleeve 19 is displaced into a position in which the second section 19B of the locking sleeve 19 surrounds the shaped element 18, then the shaped element 18 may yield radially outward, based on the central axis 8, so that it no longer projects into the recess on the tool shaft or into the interior of the hollow shaft 3 and releases the tool 4, which then can be removed from the hollow shaft 3.

At least a part of the locking sleeve 19 surrounds the outer jacket of the hollow shaft 3 and is in contact with the inside raceway 23 of the ball bearing 22, so that the locking sleeve 19 rotates together with the hollow shaft 3. Beneath the ball bearing 22, there is a ring-shaped bearing disk 47 and a spring element 25. The spring element 25, which is designed as a plate spring in particular, prestresses the locking sleeve 19 in the locking position shown in FIG. 2, in which the tool 4 is secured in the hollow shaft 3. To release the tool 4 out of the hollow shaft 3, the user must overcome the spring force of the spring element 25 to displace the locking sleeve 19 in the direction of the tool receptacle opening 16. Since the locking sleeve 19 is connected to the ball bearing 22, the ball bearing 22 and the bearing disk 47 are also arranged displaceably in the handpiece 1.

The locking sleeve 19, the ball bearing 22, the spring element 25 and the bearing disk 47 are accommodated in a cage 24 which surrounds the hollow shaft 3 and is immovably accommodated in the handpiece 1, in particularly nonrotatably. The cage 24 has a cylindrical outside wall 26 concentrically surrounding the hollow shaft 3, for example, and a bottom plate 24A with an opening for the hollow shaft 3 to pass through it. A fastening element 48, which prevents the rotation of the outer raceway 49 of the roller bearing 22, is preferably provided between the roller bearing 22 and the inside of the outside wall 26 or as an integral part of the outside wall 26. The fastening element 48 is in particular designed as a protrusion or bulge in the outside wall 26 protruding into the interior of the cage 24. Alternatively, the fastening element 48 is designed as a separate ball or separate pin between the roller bearing 22 and the inside of the outside wall 26.

Figure 4:
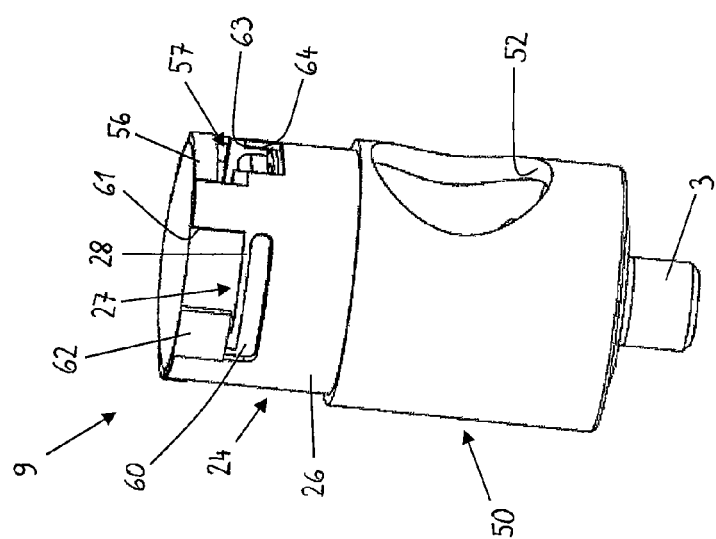
FIG. 4 shows a perspective outside view of an embodiment of the tool-holding/releasing device embodied as a cartridge-type unit, including the first coil arranged therein and the carrier for the first coil of the inductive data and power transfer unit.

As shown in FIGS. 1 and 4 in particular, the cage 24 is an integral part of a sleeve 50 or is connected to the sleeve 50. The cartridge or sleeve 50 surrounds the two roller bearings 22, 36 and the tool holding/releasing device 9 and the hollow shaft 3 and forms with these elements a cartridge-type unit, which is insertable into and/or removable from the head part 30 of the handpiece 1 via an opening situated opposite the tool receptacle opening 16. The gearwheel 34 protrudes through a bore 52 in the sleeve 50 into the head part 30 to mesh with the gearwheel 35. For support of the cartridge 50 in the interior of the head part 30, two shoulders 53 (see FIG. 1) and 54 (see FIG. 3) are provided on the inside of the outer shell 2. The shoulder 54 is part of a threaded bushing 55 which is detachably connectable to the outer shell 2 and secures the cartridge 50 in the handpiece 1 and is separated from the remaining outer shell 2 for insertion of the cartridge 50 into the handpiece 1 or for releasing the cartridge 50 therefrom.

The operating element 20 of the tool-holding/releasing device 9 made of a magnetically and electrically nonconductive material, in particular plastic or ceramic, comprises according to FIGS. 1-3 a pushbutton or a pressure cover 12. The pressure cover 12 is countersunk at least partially or completely in the outer shell 2 of the handpiece 1 and is displaceable by means of one or more guide elements 56 along the central axis 8 of the hollow shaft 3. The guide element 56 comprises, for example, a guide strip which is guided in a recess 57 in the cage wall 26 (FIG. 4). The operating element 20 or the pressure cover 12 comprises a cap 58 which seals the opening 51 and two contact elements 21. The two arc-shaped contact elements 21 are arranged on the immediate outer edge of the cap 58 and thus at a distance radially from the locking sleeve 19 or the hollow shaft 3. The two contact elements 21 are separated from one another by two recesses 59. As described below, the two contact elements 21 cooperate with the locking sleeve 19 to release the tool 4 out of the hollow shaft and/or to secure it in the hollow shaft 3. In addition, the contact elements 21 also serve to guide the pressure cover 12 in the head part 30 of the handpiece 1.

Figure 5:
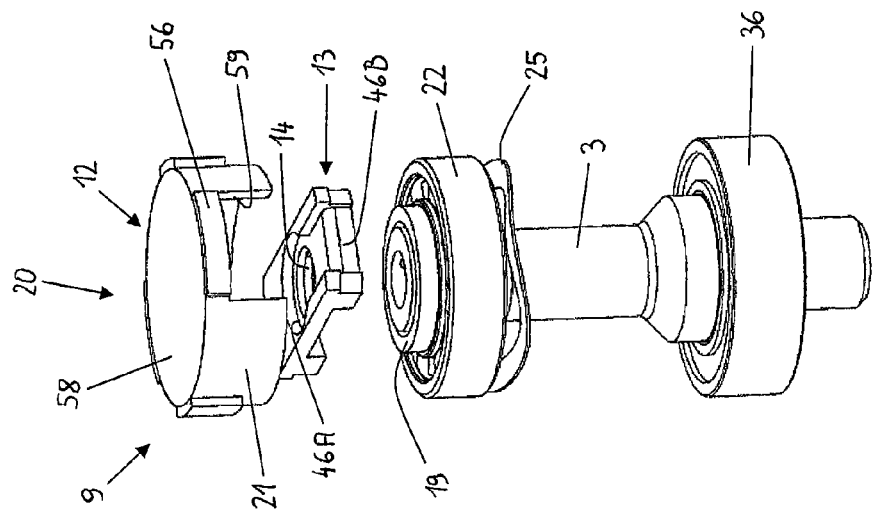
FIG. 5 shows the cartridge-type unit of FIG. 4 in an exploded diagram.

As shown in FIGS. 3 and 5 in particular, the carrier 13 of the first coil 5 has a rectangular shape, the two shorter opposing sides of the carrier 13 being of such dimensions that they can be accommodated in the recesses 59. The two contact elements 21 extend around the first coil 5 and the carrier 13 on both its longer sides and contact the roller bearing 22 with their free ends, in particular its outer raceway 49. As already described above, the roller bearing 22 is connected to the locking sleeve 19 and is prestressed by the plate spring 25, so that when the user presses on the cap 58 of the operating element 20 and displaces the operating element 20 in the direction of the tool receptacle opening 16, the locking sleeve 19 is moved out of its locking position via the contact elements 21 and the roller bearing 22. When the user releases the cap 58, the spring element 25 displaces the locking sleeve 19, the roller bearing 22 and the operating element 20 back into the locking position shown in FIG. 3.

Due to the lateral or radially outwardly displaced arrangement of the contact elements 21 in the head part 30 of the handpiece 1 and/or due to the arrangement of the contact elements 21 on the outside edge of the cap 58 of the operating element 20, and preferably additionally due to the curvature of the cap 58, a receptacle or a cavity 11 in which the first coil 5 and preferably also the carrier 13 and the memory unit 7 of the tool 4 can advantageously be accommodated is formed in the head part 30 or inside the tool-holding/releasing device 9. The cavity 11 is arranged in particular between the end 10 of the hollow shaft 3 facing the tool-holding/releasing device 9 of the handpiece 1 and the pressure cover 12 of the tool-holding/releasing device 9. The carrier 13 and the first coil 5 are thus accommodated within the tool-holding/releasing device 9 and/or parts of the tool-holding/releasing device 9 are arranged on both sides of the carrier 13 so that, as already described above, the first coil 5 in particular is protected and in addition, an especially compact design of the head part 30 is achieved.

For moving the operating element 20, in particular for displacing it into its starting position shown in FIG. 3, the handpiece 1 preferably has, in addition to the spring element 25, another spring element, which directly prestresses the operating element 20. This spring element comprises either a separate spring, in particular a spiral spring arranged beneath the operating element 20, or according to a preferred embodiment, the spring element is designed as an integral part of the cage 24, in particular of the cage wall 26 (see FIG. 4). This spring element 27 comprises one or more spring straps or spring arms 28 shaped from the cage wall 26, each spring arm 28 being separated from the remaining cage wall 26 by at least one slot 60. A recess 61 with which a protrusion 62 of the operating element 20 engages is allocated to each spring arm 28. Each protrusion 62 contacts a spring arm 28 and is supported on the spring arm 28.

It can also be seen from FIG. 4 that the recess 57 in the cage 24 has a shoulder or a stop 63 for limiting the displacement path of the operating element 20 and for supporting the carrier 13 of the first coil 5. The recess 57 becomes narrower following the shoulder 63 in the direction of the bore 52. This narrowed section 64 serves as an outlet for the electric lines 15 out of the cage 24.

Figure 6A:
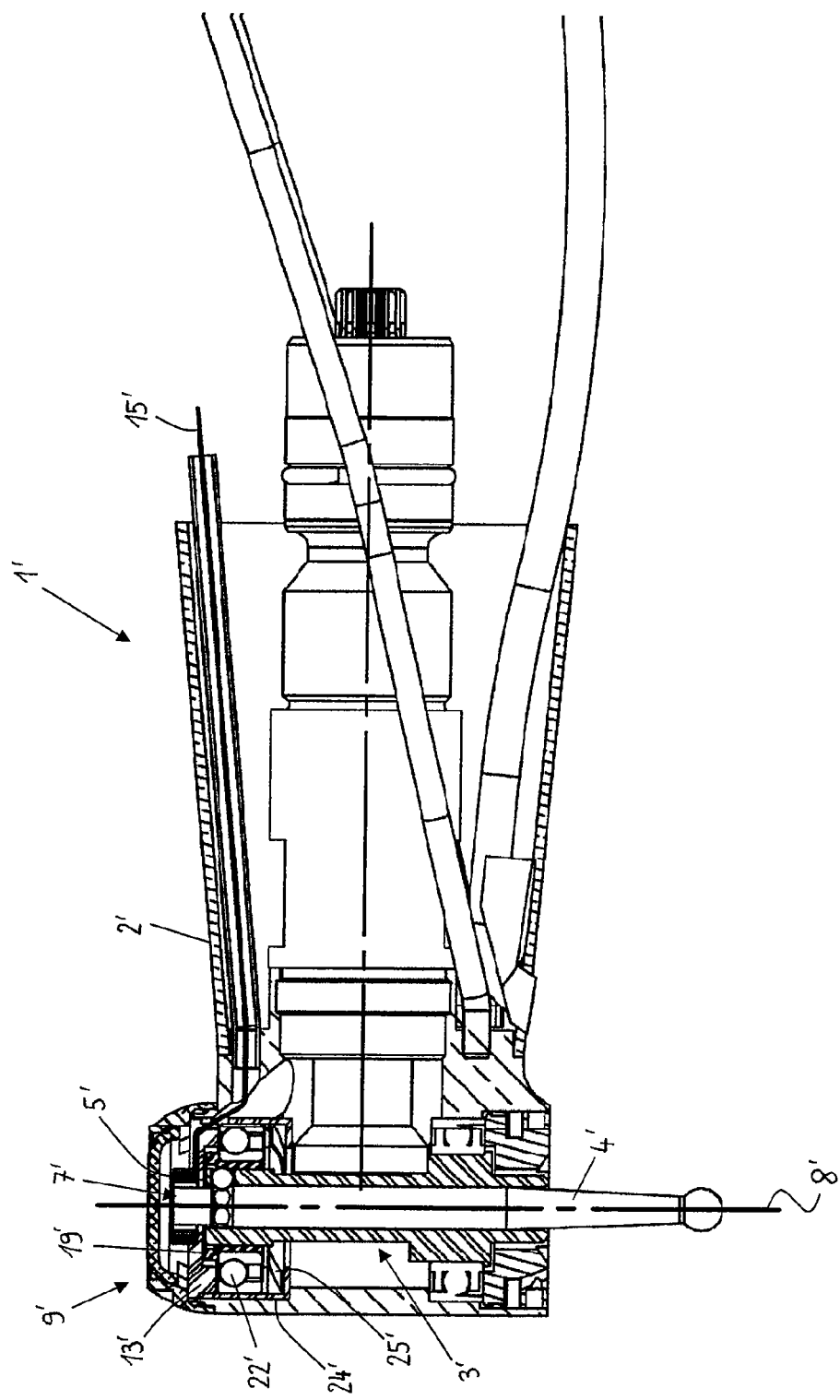
FIG. 6A shows a sectional diagram of a second embodiment of a medical or dental handpiece having an inductive data and power transfer unit and a tool-holding/releasing device.

The handpiece 1' in FIG. 6A has the same design as the handpiece 1 of FIG. 1. It also has a hollow shaft 3' with a central axis 8' to receive a treatment tool 4' with a memory unit 7', a first coil 5' supported on a carrier 13', electric lines 15' connected thereto, a tool-holding/releasing device 9' with a locking sleeve 19' and a displaceable bearing 22' connected to the locking sleeve 19' as well as a spring element 25'. The locking sleeve 19', the bearing 22' and the spring element 25' are in turn accommodated in a cage 24', which is supported in a rotationally fixed and nondisplaceable manner on the outer shell 2' of the handpiece 1'. In the embodiment according to FIG. 6, the cage 24' is a separate component, which surrounds the hollow shaft 3' but is not part of a cartridge, as in the handpiece 1 in FIG. 1.

Figure 6B:
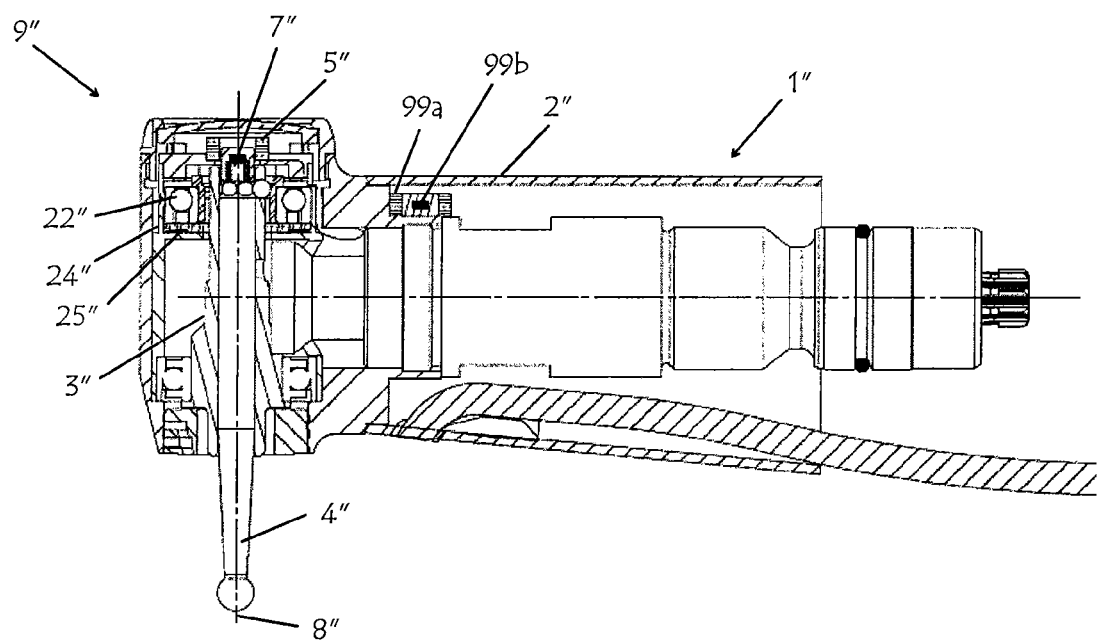
FIG. 6B shows a sectional diagram of another embodiment of a medical or dental handpiece similar to FIG. 6A, except having a second coil on the handpiece.

FIG. 6B shows a handpiece 1", which is similar to the handpiece 1' of FIG. 6A, except the handpiece 1" includes a second coil 99a on the handpiece. In the illustrated embodiment, the second coil 99a is located in the grip section of the handpiece. The second coil 99a is inductively coupleable with a memory unit 99b for handpiece data, said memory unit 99b comprising another coil, such that power transfer to the memory unit 99b and data transfer with the memory unit 99b can take place. Thus handpiece 1" has two independent data and/or energy transfer units, one transfer unit for tool data comprising the coil 5" and the memory unit 7" and another transfer unit for handpiece data comprising the coil 99a and the memory unit 99b. At least one of the transfer units may either be connected to electric wires (similar to lines 15 in FIG. 1), and/or inductively connectable, to a reading and/or sending device 100 (see FIG. 8).

Figure 7:
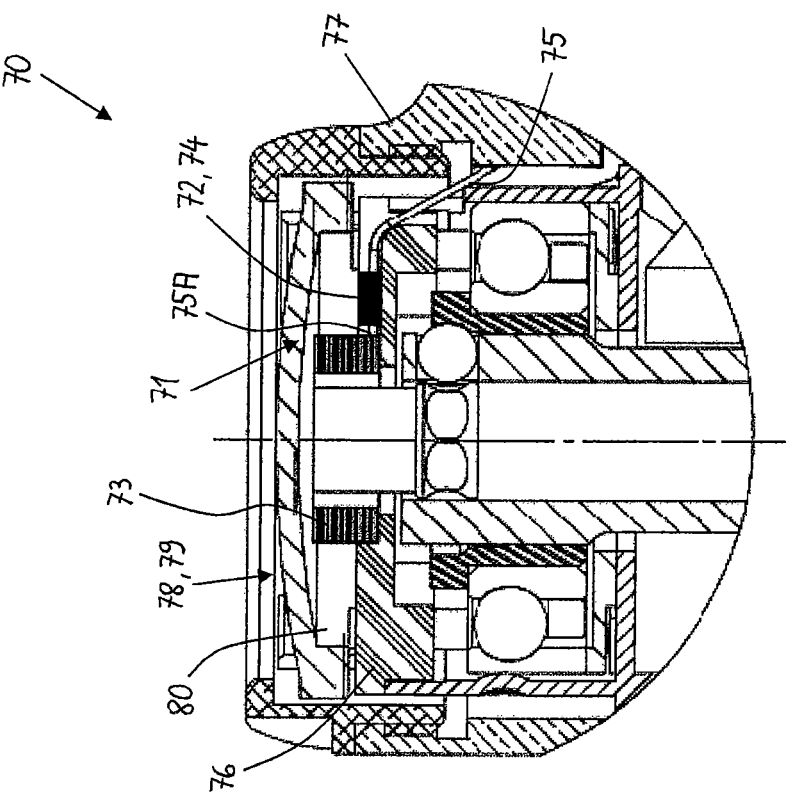
FIG. 7 shows a sectional diagram of a detail of an embodiment of a handpiece head having a memory unit with an optional inductive or hardwired power and/or data transfer.

FIG. 7 shows a detail of a handpiece and/or a handpiece head 70. The design of the handpiece and/or handpiece head 70 and the arrangement and functioning of the components of the handpiece 70, in particular the tool-holding/releasing device, the coil for inductive power and/or data transfer, the carrier element supporting the coil and the hollow shaft for receiving a treatment tool are the same as those shown in FIGS. 1-5 and specified in the accompanying description, so that they need not be discussed further again.

In contrast with the handpiece shown in FIGS. 1-5, the handpiece 70 is provided with a memory unit 71, comprising a memory element 72 for storage of operational and/or identification data of the handpiece 70, a first coil 73 provided on the handpiece 70 and connected to the memory element 72 and a read and/or write device 74 connected to the memory element 72 for reading out and/or writing to the memory element 72 operational and/or identification data. The memory unit 71 is connected by two electric lines 75 to the coupling device of the handpiece 70, by which a connection to the control and/or supply unit of the handpiece 70 can be established. Two electric lines 75A connect the memory element 72 and the read and/or write device 74 to the first coil 73. The memory unit 71 and the lines 75, 75A are arranged on a single carrier element 76.

For readout of data from the memory unit 72 or for storing data on the memory element 72 as well as for transmitting the power supply, two options are thus available to the user: The power and/or data transfer may take place either in a hardwired process via the electric lines 75, 75A, which receive power, in particular electric power from the controller and/or supply unit or directly from a power source and/or which are or can be connected to a controller, in particular a microcomputer, of the control and/or supply unit and send the data to the controller and/or receive data from the controller.

Alternatively, the power and/or data transfer to or from the memory element 72 is performed inductively via the first coil 73. To do so, the handpiece 70 must be brought into proximity to a reading and/or sending device 100 (see FIG. 8), such that an inductive coupling of the first coil 73 with an additional coil 101 of the reading and/or sending device 100 occurs.

It is of course also possible to use both transmission pathways simultaneously for power and/or data transfer. For example, the memory unit 71 may be supplied with power over electric lines 75, 75A, while at the same time an inductive data transfer takes place between the reading and/or sending device 100 and the handpiece 70. Alternatively, an inductive power transfer may take place between the reading and/or sending device 100 and the handpiece 70, and a hardwired data exchange may take place over line 75, which may also be embodied as an optical conductor according to this embodiment.

To increase the quality of the inductive data exchange between the first coil 73 and the reading and/or sending device 100, the handpiece 70 has at least one of the following features:

At least one section of the outer shell 77 of the handpiece 70, in particular the section of the outer shell 77 which surrounds the first coil 73 provided on the handpiece 70 comprises a magnetically and electrically nonconductive material, in particular plastic, glass or ceramic. Preferably the operating element 78 of the tool-holding/releasing device, in particular the pressure cover 79, comprises an electrically nonconductive material.

The first coil 73 is arranged on the outer shell 77 or adjacent to the outer shell 77 or at least partially in the outer shell 77.

The first coil 73 provided on the handpiece 70 is surrounded by an electric insulation layer, which comprises in particular at least one air gap 80 around the first coil 73, an operating element 78 of the tool-releasing device, comprising an electrically nonconductive material or a carrier element 76 comprising an electrically nonconductive material.

Figure 8:
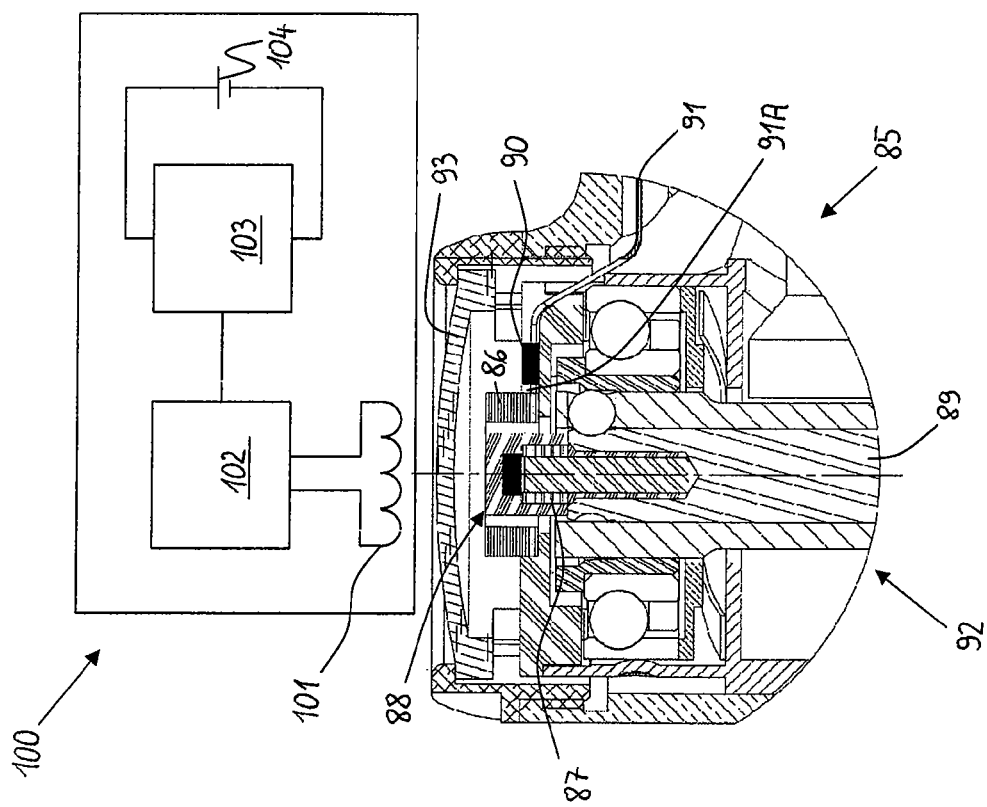
FIG. 8 shows a schematic diagram of an embodiment of a reading and/or sending device and a detail of an embodiment of a handpiece head having a single coil by means of which the tool-related data and handpiece-related data are transferable inductively to the reading and/or sending device.

The detail of a handpiece and/or of a handpiece head 85 shown in FIG. 8 represents a combination of the handpiece 1 of FIGS. 1-5 and the handpiece 70 of FIG. 7. The handpiece 85 thus comprises in particular a first coil 86 for inductive coupling, in particular for inductive power and/or data exchange, with a memory unit 88 of the treatment tool 89, comprising a second coil 87 for storage of tool-related data and a memory element 90 provided in the handpiece 85 for storage of handpiece-related data. The first coil 86 is electrically connected to the memory element 90 via electric lines 91A.

In addition to the coil 101 for inductive coupling with the coil 86 of the handpiece 85, the reading and/or sending device 100 comprises a signal amplifier 102, preferably bidirectional, for the inductively transferable data, a signal processing unit 103 and a power source 104 or a connection to a power source. In FIG. 8, the handpiece 85 and the reading and/or sending device 100 are arranged so close to one another that there is an inductive coupling for power and/or data transfer between the coil 86 of the handpiece 85 and the coil 101 of the reading and/or sending device 100. Due to the fact that the coil 87 of the treatment tool is accommodated in the coil 86 of the handpiece 85, these two coils 86, 87 are also inductively coupled for power and/or data transfer.

The memory element 90 of the handpiece 85 is embodied as a writable memory, which temporarily stores tool-related data in particular during its transfer between the reading and/or sending device 100 and the memory unit 88 of the treatment tool 89. The electric lines 91 supply the memory element 90, the coil 86 and the memory unit 88 of the tool 89 with electric power in a hardwired system. Based on the arrangement of the coil 86 of the handpiece 85 at the connecting device 92 for the treatment tool 89 and close to the outer shell of the handpiece 85, in particular beneath the operating element 93 of the tool-releasing device, as well as on the basis of the electric connection between coil 86 and the memory element 90, it is possible to inductively transmit the tool-related data as well as the handpiece-related data over the first coil 86. The transfer of tool-related data and handpiece-related data, in particular sequential or optional, is preferably controlled by a control device, which is part of the reading and/or sending device 100, of the handpiece 85 and/or of the control and/or power supply unit of the handpiece 85.

Figure 9:
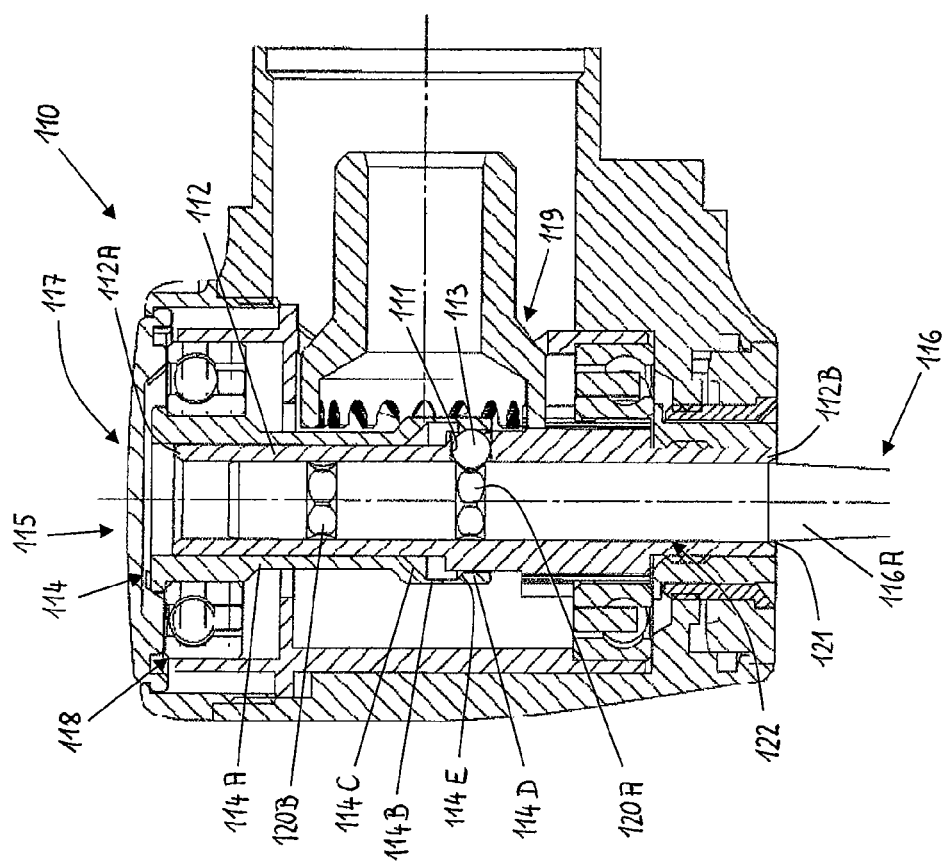
FIG. 9 shows an alternative embodiment of a tool-holding/releasing device for securing and/or releasing the treatment tool in the handpiece and a treatment tool having two recesses in the tool shaft for inserting the treatment tool to different depths in the tool-holding/releasing device.

The design of the tool-holding/releasing device 117 of the medical, in particular dental, handpiece 110 shown in FIG. 9 corresponds in many features to the tool-holding/releasing device 9 of FIGS. 2 and 3, so that in the following discussion, mainly the additional features or the features and properties of the tool-holding/releasing device 117 differing from those of the tool-holding/releasing device 9 are described below.

The tool-holding/releasing device 117 comprises one or more, in particular three, shaped elements 113 passing through the bores 111 in the hollow shaft 112 and protruding through the bores 111 into the interior of the hollow shaft 112, a movably arranged locking sleeve 114 cooperating with the shaped element 113 and an operating element 115 cooperating with the locking sleeve 114 for moving the locking sleeve 114. The shaped elements 113 are embodied as spheres, hemispheres, ellipsoids or cylinders, for example.

The locking sleeve 114 surrounds the hollow shaft 112 and is axially displaceable along the central axis of the hollow shaft 112. The locking sleeve 114 has a first section 114A with a first inside diameter and a second section 114B with a second larger inside diameter, so that the second section 114B is at a greater distance from the outer jacket of the hollow shaft 3 than the first section 114A. The two sections 114A, 114B are joined together by a short conical section 114C. Section 114B is connected to a conical section 114E and another section 114D whose inside diameter is smaller than the inside diameter of section 114B. As shown in FIG. 9, section 114D presses the shaped element 113 into the bore 111 for axially attaching the tool 116 in the hollow shaft 112 and for transferring the torsional moment to the tool 116, so that a part of the shaped element 113 protrudes into the interior of the hollow shaft 112 and the shaped element 113 comes in contact with the tool 116, in particular in one or more recesses 120A, 120B on the tool shaft. If the locking sleeve 114 is displaced into a position in which the second section 114B surrounds the shaped element 113, the shaped element 113 can yield radially to the outside, based on the central axis, so that it no longer protrudes into the recesses 120A, 120B on the tool shaft or into the interior of the hollow shaft 112 and releases the tool 116 for removal from the hollow shaft 112.

At least a part of the elongated tubular locking sleeve 114 surrounds the outer jacket of the hollow shaft 112 and is in contact by a shoulder with the inside raceway of the roller bearing 118 so that the locking sleeve 114 rotates together with the hollow shaft 112. The two sections 114B and 114D surround the hollow shaft 112 in an area between its two ends 112A, 112B, for example approximately in the area of the half of the longitudinal extent of the hollow shaft 112. Accordingly, the bore 111 and the shaped element 113 are also a distance away from the end areas 112A, 112B of the hollow shaft 112. In particular the sections 114B, 114D are arranged between the outer jacket of the hollow shaft 112 and the drive element 119 of the handpiece 10, which induces the hollow shaft 112 to motion, e.g., the gearwheel of the drive element 119.

The treatment tool 116 comprises, in addition to a treatment section, a shaft section 116A on which at least two contact faces 120A, 120B arranged a distance apart from one another axially, e.g., receptacles, punctures, recesses or indentations, are provided for engagement of the at least one shaped element 113. The recesses 120A, 120B may surround the shaft section 116A in a ring shape or in a semicircle and/or may have cups, for example. The treatment tool 116 thus forms a medical, in particular dental, treatment unit with the tool-holding/releasing device 117, making it possible for the user to shift the treatment tool 116 into the hollow shaft 112 to different depths and thus to vary the length of the section of the treatment tool 116 protruding out of the handpiece 110 and/or out of the handpiece head. The treatment tool 116 may thus be secured in handpiece head 110 optionally in a first insertion position, in which the shaped element 113 engages in the receptacle 120B, or in a second insertion position, in which the shaped element 113 engages in the receptacle 120A. In order for the treatment tool 116 to be held reliably and securely in the headpiece head, in particular in the first insertion position in which a longer section of the treatment tool 116 protrudes out of the handpiece head 110, the hollow shaft 112 forms a one-piece tool seat 122 extending continuously from the operating element 115 or from the drive element 119 to the tool receptacle opening 121.

Figure 10A:
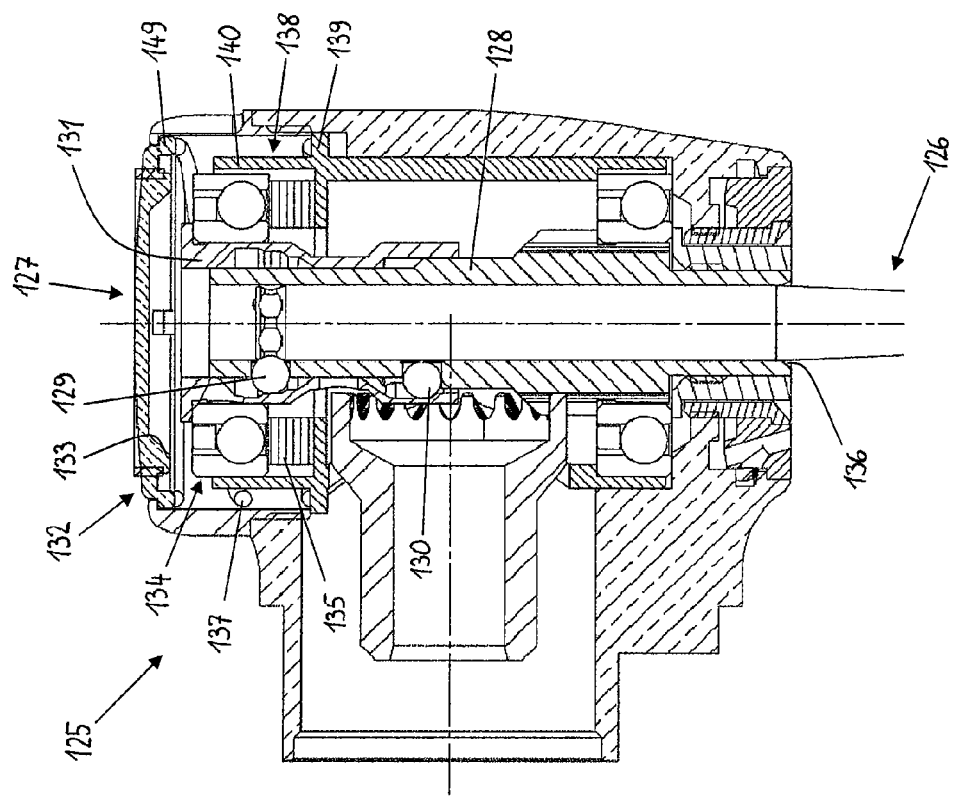
FIGS. 10A-10C show an alternative embodiment of a tool-holding/releasing device for securing and/or releasing the treatment tool in the handpiece with two independent holding devices for the treatment tool and a treatment tool for inserting the treatment tool to different depths into the tool-holding/releasing device.
Figures 10B, 10C:
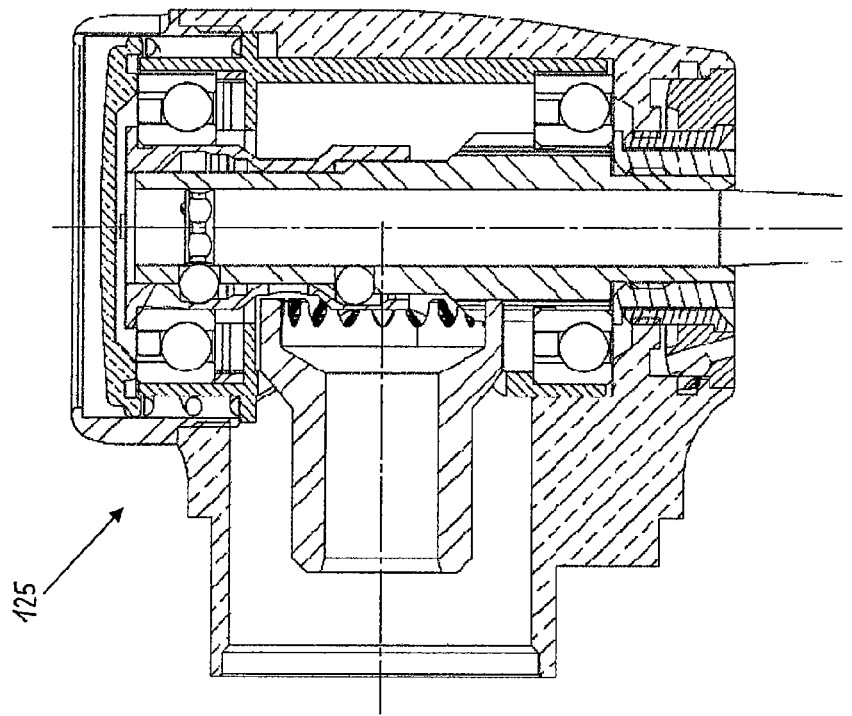

FIGS. 10A-10C show an alternative embodiment of a handpiece 125 whose tool-holding/releasing device 127 is also designed so that the treatment tool 126 can be inserted into the tool-holding releasing device 127 to different depths. FIG. 10A shows the tool 126 in a first position in which it is inserted deep into the hollow shaft 128 of the tool-holding/release device 127. FIG. 10B shows the tool 126 in a second position, in which it is inserted into the hollow shaft 128 of the tool-holding/releasing device 127 to a lesser depth than in FIG. 10A, so that a longer section of the treatment tool 126 protrudes out of the handpiece 125 and/or out of the handpiece head. FIG. 10C shows the tool-holding/releasing device 127 in its unlocked position, so that the treatment tool 126 is removable from the hollow shaft 128, for example, or is displaceable into the second position according to FIG. 10B.

The basic design of the tool-holding/releasing device 127 of the medical, in particular dental, handpiece 125 shown in FIGS. 10A-10C corresponds in many features to the tool-holding/releasing device 9 of FIGS. 2 and 3 or the tool-holding/releasing device 117 of FIG. 9, so that mainly the additional or different features and properties of the tool-holding/releasing device 127 are described below.

The tool-holding/releasing device 127 comprises several shaped elements 129, 130 protruding into the interior of the hollow shaft 128, a locking sleeve 131 that is arranged movably and cooperates with the shaped elements 129, 130 and an operating element 132 that cooperates with the locking sleeve 131 for moving or displacing the locking sleeve 131. The shaped elements 129, 130 are designed, for example, as spheres, hemispheres, ellipsoids or cylinders. The shaped elements 129, 130 designed as spheres or their spherical ends preferably have the same radius.

As was the case with the tool-holding/releasing devices 9 and 117 of the previous embodiments, the user moves the locking sleeve 131 by pressing on the operating element 132 whose at least one protrusion or at least one contact element 133 comes in contact with the roller bearing 134, in particular its outer raceway, and displaces it against the force of a spring element or spring package 135 in the direction of the tool receptacle opening 136. The locking sleeve 131 connected to the roller bearing 134 is therefore also displaced in the direction of the tool receptacle opening 136 (see FIG. 10C). If the operating element 132, which is preferably designed as a pressure cover or pushbutton, is released, the spring package 135 displaces the roller bearing 134 and the locking sleeve 131 automatically into the direction of the operating element 132 (see FIG. 10A or 10B). The operating element 132 is also moved back into its starting position by another spring element 137.

The spring element 137 is mounted on a cage 138 to accommodate the spring package 135 and the roller bearing 134, in particular on a shoulder 139 of the cage 138, which is separated from the spring package 135 and the roller bearing 134 by an annular wall 140. The spring element 137 comes in contact with the operating element 132 on its outer circumference, in particular on a ring-shaped shoulder 149 provided there. This shoulder 149 also serves as a guide element along the inside wall of the housing of the handpiece 125. The protrusion 133 is, according to this embodiment, spaced a distance away from the immediate outside circumference of the operating element 132 or the annular wall 140 or, based on the central axis of the tool-holding/releasing device 127, is arranged radially away from the locking sleeve 131 or between the spring element 137 and the locking sleeve 131.

For positioning the treatment tool 126 in different positions or depths of insertion in the hollow shaft 128, the handpiece 125 has at least two separate holding units 141, 142 spaced a distance apart from one another axially. Each holding unit 141, 142 comprises one or more, preferably three shaped elements 129, 130, which are designed as spheres, hemispheres, ellipsoids, cylinders or pins, for example, and one or more bores 145, 146 in the hollow shaft 128, whereby the number of bores 145, 146 corresponds in particular to the number of shaped elements 129, 130. The shaped elements 129, 130 penetrate through the bores 145, 146 and protrude through the bores 145, 146 into the interior of the hollow shaft 128 to contact a contact surface 147 of the treatment tool 126, e.g., in the form of a receptacle, a puncture, a recess or an indentation, and thereby to secure the treatment tool 126 axially in the hollow shaft 128 and transmit a torsional moment to the treatment tool 126. One of the two holding devices 141, 142 is preferably arranged between the outer jacket of the hollow shaft 128 and the drive element 148 of the handpiece 125 which induces motion in the hollow shaft 128, e.g., the gearwheel of the drive element 148.

The treatment tool 126 has a working or treatment section and a shaft section 126A on which the single contact face 147 is provided. The contact face 147 surrounds, for example, the shaft section 126A in a ring shape or in a semicircle and/or has cups. The contact face 147 is preferably arranged directly on the end of the treatment tool 126. By insertion of the contact face 147 into the hollow shaft 128 optionally up to the first holding unit 141 or to the second holding unit 142, the insertion position or depth of insertion of the treatment tool 126 and/or the length of the section of the treatment tool 126 protruding out of the handpiece head 125 can be defined by the user.

Figure 11:
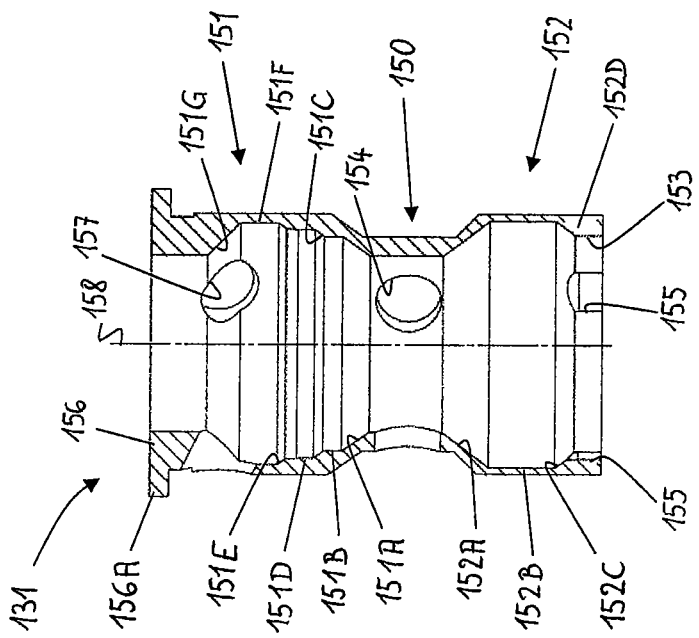
FIG. 11 shows an embodiment of a locking sleeve of the tool-holding/releasing device of FIGS. 10A-10C.

The design of the locking sleeve 131 which is responsible for the fixation and release of the treatment tool 126 is shown in FIG. 11 in particular. The locking sleeve 131 has an elongated hollow or tubular shape. The locking sleeve 131 comprises a central section 150 and two sections 151, 152 connected to opposite ends of the central section 150 to receive one shaped elements 129, 130 each. The locking sleeve 131 and/or the three sections 150, 151, 152 are penetrated by a bore 153 which has different inside diameters due to the difference in inside diameters of the central section 150 and the two sections 151, 152. The bore 153 serves to receive the hollow shaft 128 so that the locking sleeve 131 surrounds the hollow shaft 128 and is axially displaceable along the central axis of the hollow shaft 128.

At least one bore or opening 154 for passage of lubricant between the locking sleeve 131 and the hollow shaft 128 is provided on the central section 150.

The section 151 has a conical transitional area 151A to the central section 150, a section 151B having a larger inside diameter in comparison with the central section 150, a conical area 151C, a section 151D having a larger inside diameter in comparison with section 151B, a conical section 151E, a section 151F having a larger inside diameter in comparison with section 151D, and a conical transitional area 151G to a connecting section 156 of the locking sleeve 131. The connecting section 156 connects the locking sleeve 131 to the roller bearing 134 and therefore has in particular a ring flange 156A protruding radially away from the locking sleeve 131. In addition, one or more mounting openings 157 are provided in section 151 in particular in the conical transitional area 151G, to facilitate the installation of the shaped elements 129 in the bores 145.

The section 152 has a conical transitional area 152A to the central section 150, a section 152B with a larger inside diameter in comparison with the central section 150, a narrow conical section 152C and a section 152D with a smaller inside diameter in comparison with section 152B. One or more punctures or recesses 155 are provided on section 152D, where the number of punctures 155 corresponds in particular to the number of shaped elements 130.

As described below, the conical sections 151A, 151C, 151E, 151G, 152A and 152C form bearing sites or ring shoulders in the interior of the bore 153 for bearing support of the shaped elements 129, 130: When the treatment tool 126 assumes its deep insertion position, as illustrated in FIG. 10A, the shaped element 129 is supported on the conical section 151C and is pressed by this section 151C and the cylindrical section 151D through the bore 145 into the receptacle 147 of the treatment tool 126. At the same time, the shaped element 130 is pressed by the conical section 152C on which it is supported and by the cylindrical section 152B into the bore 146, so that it is at least secured therein and, if necessary, also comes in contact with the shaft section 126A. Since for fixation of the treatment tool 126 in this deep insertion position, the shaped element 129 protrudes farther into the hollow shaft 128 than the shaped element 130, or the shaped element 129 is arranged closer to the central axis of the hollow shaft 128 than the shaped element 130, the inside diameter of the section 151D is smaller than the inside diameter of section 152B.

With the insertion position illustrated in FIG. 10B, in which a longer part of the treatment tool 126 protrudes out of the handpiece 125, the shaped element 130 is pressed by the cylindrical section 152D through the bore 146 into the receptacle 147 of the treatment tool 126. The shaped element 129 is supported on section 151A and is affixed by this conical section 151A and by the cylindrical section 151B in the bore 145. A part of the shaped element 129 protrudes into the interior of the hollow shaft 128 without coming in contact with the treatment tool 126. The inside diameter of the section 152D and the section 151B are approximately equal. The axial distance (based on the central axis 158 of the locking sleeve 131) between the cylindrical section 152D and the cylindrical section 151D, which depending on the depth of penetration press the shaped elements 129, 130 into the receptacle 147 of the treatment tool 126 is greater than the axial distance of the midpoints or longitudinal axes of the two shaped elements 129, 130.

To release the treatment tool 126 out of its insertion positions, the shaped elements 129, 130 and the receptacle 147 of the treatment tool 126 are disengaged (see FIG. 10C). For that the shaped element 129 is in sections 151E and 151F, and the shaped element 130 is in section 152B. The cylindrical sections 151F and 152B thus have approximately the same inside diameter and are the same distances apart from one another axially as the midpoints or longitudinal axes of the two shaped elements 129, 130.

Each of punctures 155 in the cylindrical section 152D receives a shaped element 130. The punctures 155 and the shaped elements 130 form an entraining element, which ensures that the locking sleeve 131 will rotate with the hollow shaft 128, in particular when the handpiece 125 is operated, and the hollow shaft 128 is set in rotation without a tool 126 being accommodated in the hollow shaft 128. The distance between the cylindrical section 151D and the central axis 158 of the locking sleeve 131 is approximately the same as the distance between the bottom of the puncture 155 and the central axis 158. Accordingly, the inside diameter of the cylindrical section 151D is larger than the inside diameter of the cylindrical section 152D with its three punctures 155.

According to one embodiment, the handpiece heads 110 and 125 in FIGS. 9 and 10A-10C may of course be provided with a coil for inductive coupling to a memory unit of a treatment tool comprising a second coil. The coil is preferably provided on, at or around the respective hollow shaft 112, 128 of the handpiece heads 110, 125, especially preferably the coil is arranged within or beyond of the axial extent of the hollow shafts 128 and within the radial extent of the hollows shafts 112, 128.

The invention is not limited to the embodiments described here but instead comprises all embodiments, which employ or include the basic appropriate function principle of the invention. In addition, all features of all the embodiments described and illustrated here may be combined with one another.

What is claimed is:

1. A medical or dental handpiece comprising:
   a handheld outer housing;
   a driveable hollow shaft shaped to receive a treatment tool, the driveable hollow shaft being arranged in the outer housing and driveable relative to the outer housing to move the treatment tool;
   a first coil for inductive coupling with a memory unit of the treatment tool comprising a second coil, the first coil comprising a conductive component;
   wherein the driveable hollow shaft which is driveable relative to the outer housing extends along a central axis and has an axial extent and radial extent, based on the central axis, and
   wherein the first coil is arranged beyond the axial extent of the driveable hollow shaft and wherein at least a part of the conductive component of the first coil is arranged within the radial extent of the driveable hollow shaft which is driveable relative to the outer housing.

2. The medical or dental handpiece according to claim 1, wherein
   the first coil is arranged in a cavity between an end of the driveable hollow shaft facing the tool-holding/releasing device and a pressure cover or a cap of a tool-holding/releasing device of the medical or dental handpiece.

3. The medical or dental handpiece according to claim 1, wherein
   the conductive component of the first coil is surrounded by an electric insulation layer which comprises at least one of an air gap around the conductive component, an operating element of a tool-holding/releasing device comprising an electrically nonconductive material or a carrier supporting the conductive component and comprising an electrically nonconductive material.

4. The medical or dental handpiece according to claim 1, further comprising:
   a carrier which supports the first coil, wherein said carrier has an opening around which the first coil is arranged, the opening being dimensioned such that the opening can accommodate at least partially the memory unit of the treatment tool so that the first coil and the second coil of the memory unit can be arranged adjacent each other.

5. A medical or dental handpiece comprising:
   a handheld outer housing;
   a hollow shaft and a treatment tool received in the hollow shaft, the hollow shaft being arranged in the outer housing and driveable relative to the outer housing to move the treatment tool;
   a first coil for inductive coupling, the treatment tool comprising a second coil for inductive coupling with the first coil;
   wherein the hollow shaft extends along a central axis and has an axial extent and radial extent, based on the central axis,
   wherein the hollow shaft comprises a second end at a tool receptacle opening of the handheld outer housing and a first end opposite the second end which faces a cap or pressure cover of a tool-holding/releasing device of the handpiece,
   wherein, when the treatment tool is received in the hollow shaft, at least a portion of the second coil of the treatment tool is arranged beyond the axial extent of the hollow shaft in a space defined by or below the cap or pressure cover of a tool-holding/releasing device, and
   wherein the first coil is arranged at the first end of the hollow shaft for inductive coupling with the second coil of the treatment tool for power and/or data transfer between the first coil and the second coil.

6. The medical or dental handpiece according to claim 5, wherein
   the treatment tool comprises a memory unit comprising the second coil and a memory storing treatment tool related data.

7. The medical or dental handpiece according to claim 6, comprising:
   a carrier which supports the first coil, wherein said carrier has an opening around which the first coil is arranged, the opening being dimensioned such that the opening can accommodate at least partially the memory unit of the treatment tool so that the first coil and the second coil of the memory unit can be arranged adjacent each other.

8. The medical or dental handpiece according to claim 7, wherein
   the opening of the carrier and the first coil are arranged concentrically with the central axis of the hollow shaft.

9. The medical or dental handpiece according to claim 5, wherein
the first coil is connected to at least one line for power and/or data supply.

10. The medical or dental handpiece according to claim 5, wherein
the pressure cover or cap of the tool-holding/releasing device comprises at least one of a ceramic, plastic or glass material.

11. The medical or dental handpiece according to claim 5, wherein
the second coil of the treatment tool is arranged at a proximal end of the treatment tool opposite a distal treatment end of the treatment tool.

12. A medical or dental handpiece comprising:
a handheld outer housing;
a connecting device for connection of a treatment tool which is arranged in the outer housing and inducible to a driving movement, wherein the connecting device comprises a hollow shaft shaped to receive the treatment tool, the hollow shaft being driveable relative to the outer housing to move the treatment tool;
a tool-holding/releasing device for holding and releasing the treatment tool in the hollow drivable shaft of the connecting device, said tool-holding/releasing device having a pressure cover or a cap;
a coupling device for connection of the handpiece to a control and/or power supply unit; and
a handpiece coil arranged at or adjacent the connecting device, said handpiece coil being configured for inductive coupling with a memory unit of the treatment tool comprising a treatment tool coil for storage of tool-related data, wherein
the handpiece coil is accommodated between an end of the connecting device facing the pressure cover or cap and the pressure cover or cap in a cavity defined by or beneath the pressure cover or cap.

13. The medical or dental handpiece according to claim 12, further comprising
a memory element provided in the handpiece and electrically connected to the handpiece coil for storage of handpiece related data and/or tool-related data which are supplied from the handpiece coil.

14. The medical or dental handpiece according to claim 13, comprising
a hardwired power supply for the memory element and for the handpiece coil through electric lines extending from the coupling device.

15. The medical or dental handpiece according to claim 12, wherein
the connecting device extends along a central axis and has an axial extent and a radial extent, based on the central axis, and wherein the handpiece coil is arranged beyond the axial extent of the connecting device and at least partially within the radial extent of the connecting device.

16. The medical or dental handpiece according to claim 12, wherein
the handpiece coil is surrounded by an electric insulation layer, which comprises at least one of an air gap around the handpiece coil, an operating element of the tool-releasing device comprising electrically nonconductive material and a carrier element for supporting the handpiece coil comprising electrically nonconductive material.

17. The medical or dental handpiece according to claim 12, wherein
the hollow shaft which is driveable relative to the outer housing comprises a second end at a tool receptacle opening of the outer housing of the medical or dental handpiece and a first end opposite the second end which faces the tool-holding/releasing device of the handpiece, wherein the handpiece coil is arranged at or adjacent the first end of the hollow shaft.

18. The medical or dental handpiece according to claim 12, wherein
the pressure cover or cap of the tool-holding/releasing device comprises at least one of a ceramic, plastic or glass material.

19. The medical or dental handpiece according to claim 12, comprising
a carrier which supports the handpiece coil, wherein said carrier has an opening around which the handpiece coil is arranged, the opening being dimensioned such that the opening can accommodate at least partially the memory unit of the treatment tool so that the handpiece coil and the treatment tool coil of the memory unit can be arranged adjacent each other.

20. A medical or dental treatment device comprising:
a medical or dental handpiece according to claim 12 and a reading and/or sending device with a reading and/or sending device coil, which is inductively couplable with the handpiece coil provided on the handpiece for power and/or data transfer.

21. A medical or dental treatment device comprising:
a medical or dental handpiece according to claim 12 and a treatment tool with a memory unit comprising a treatment tool coil for storage of tool-related data.

22. The medical or dental treatment device according to claim 21, wherein
the treatment tool coil is arranged at or on an end of the treatment tool opposite a treatment section of the treatment tool.

* * * * *